United States Patent
Smith et al.

(10) Patent No.: US 11,684,712 B2
(45) Date of Patent: *Jun. 27, 2023

(54) AMBULATORY INFUSION PUMPS AND RESERVOIR ASSEMBLIES FOR USE WITH SAME

(71) Applicant: MEDTRONIC MINIMED, INC., Northridge, CT (US)

(72) Inventors: Roger E. Smith, Ivins, UT (US); Mogens Bach Rasmussen, Struer (DK)

(73) Assignee: MEDTRONIC MINIMED, INC., Northridge, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 16/944,207

(22) Filed: Jul. 31, 2020

(65) Prior Publication Data

US 2020/0360600 A1   Nov. 19, 2020

Related U.S. Application Data

(63) Continuation of application No. 15/042,093, filed on Feb. 11, 2016, now Pat. No. 10,737,016.

(60) Provisional application No. 62/117,565, filed on Feb. 18, 2015.

(51) Int. Cl.
*A61M 5/142*   (2006.01)
*A61M 5/145*   (2006.01)
*A61M 5/315*   (2006.01)

(52) U.S. Cl.
CPC ...... *A61M 5/14244* (2013.01); *A61M 5/1452* (2013.01); *A61M 5/31513* (2013.01); *A61M 2005/14264* (2013.01)

(58) Field of Classification Search
CPC ............ A61M 5/14244; A61M 5/1452; A61M 5/31513; A61M 2005/3121; A61M 2005/3101
See application file for complete search history.

(56) References Cited

U.S. PATENT DOCUMENTS

| | | |
|---|---|---|
| 1,771,219 A | 7/1930 | Hein |
| 2,627,270 A | 2/1953 | Glass |
| 3,354,882 A | 11/1967 | Coanda |
| 3,662,753 A | 5/1972 | Tassell |
| 3,701,345 A | 10/1972 | Heilman et al. |
| 3,940,027 A | 2/1976 | Marterer |
| 4,116,240 A | 9/1978 | Glass |
| 4,206,764 A | 6/1980 | Williams |

(Continued)

FOREIGN PATENT DOCUMENTS

| | | |
|---|---|---|
| CA | 2406026 | 10/2002 |
| CA | 2741716 | 9/2003 |

(Continued)

OTHER PUBLICATIONS

CN Application No. 201780023000.5 Second Office Action dated Oct. 14, 2021 (with English Translation), 14 pages (MD50012USD).

(Continued)

*Primary Examiner* — Katherine H Schwiker
*Assistant Examiner* — Hong-Van N Trinh
(74) *Attorney, Agent, or Firm* — Fortem IP LLP

(57) ABSTRACT

Ambulatory infusion pumps, medicament reservoirs, and plungers, including both dynamic and static seals, plus related components, as well as component combinations and related methods.

6 Claims, 12 Drawing Sheets

(56) References Cited

U.S. PATENT DOCUMENTS

| | | |
|---|---|---|
| 4,379,453 A | 4/1983 | Baron |
| 4,529,401 A | 7/1985 | Leslie et al. |
| 4,731,058 A | 3/1988 | Doan |
| 4,767,378 A | 8/1988 | Obermann |
| 4,886,499 A | 12/1989 | Cirelli et al. |
| 4,985,015 A | 1/1991 | Obermann et al. |
| 5,176,662 A | 1/1993 | Bartholomew et al. |
| 5,244,461 A | 9/1993 | Derlein |
| 5,257,980 A | 11/1993 | Van Antwerp et al. |
| 5,259,808 A | 11/1993 | Garr |
| 5,281,111 A | 1/1994 | Plambeck et al. |
| 5,355,067 A | 10/1994 | Tabuchi |
| 5,364,242 A | 11/1994 | Olsen |
| 5,364,510 A | 11/1994 | Carpio |
| 5,378,126 A | 1/1995 | Abrahamson et al. |
| 5,380,314 A | 1/1995 | Herweck |
| 5,505,709 A | 4/1996 | Funderbunrk et al. |
| 5,530,999 A | 7/1996 | Barnes |
| 5,531,697 A | 7/1996 | Olsen et al. |
| 5,549,583 A | 8/1996 | Sanford et al. |
| 5,584,813 A | 12/1996 | Livingston et al. |
| 5,586,868 A | 12/1996 | Lawless et al. |
| 5,665,065 A | 9/1997 | Coleman et al. |
| 5,695,473 A | 12/1997 | Olsen |
| 5,779,665 A | 7/1998 | Mastrototaro et al. |
| 5,816,779 A | 10/1998 | Lawless et al. |
| 5,851,197 A | 12/1998 | Marano et al. |
| 5,858,001 A | 1/1999 | Tsals et al. |
| 5,935,106 A | 8/1999 | Olsen |
| 5,951,521 A | 9/1999 | Mastrototaro et al. |
| 5,954,696 A | 9/1999 | Ryan |
| 5,984,894 A | 11/1999 | Poulsen et al. |
| 6,033,377 A | 3/2000 | Rasmusser |
| 6,056,718 A | 5/2000 | Funderburk et al. |
| 6,093,172 A | 7/2000 | Funderburk et al. |
| 6,224,577 B1 | 5/2001 | Dedola et al. |
| 6,248,093 B1 | 6/2001 | Moberg |
| 6,254,586 B1 | 7/2001 | Mann et al. |
| 6,293,925 B1 | 9/2001 | Safabash et al. |
| 6,296,907 B1 | 10/2001 | Viksne |
| 6,362,591 B1 | 3/2002 | Moberg |
| 6,458,102 B1 | 10/2002 | Mann et al. |
| 6,461,331 B1 | 10/2002 | Antwerp et al. |
| 6,482,186 B1 | 11/2002 | Douglas et al. |
| 6,520,930 B2 | 2/2003 | Critchlow et al. |
| 6,520,938 B1 | 2/2003 | Funderburk et al. |
| 6,537,251 B2 | 3/2003 | Klitmose |
| 6,585,695 B1 | 7/2003 | Adair et al. |
| 6,585,698 B1 | 7/2003 | Packman et al. |
| 6,607,509 B2 | 8/2003 | Bobroff et al. |
| 6,629,949 B1 | 10/2003 | Douglas |
| 6,641,566 B2 | 11/2003 | Douglas et al. |
| 6,659,980 B2 | 11/2003 | Shekalim |
| 6,656,158 B2 | 12/2003 | Mahoney et al. |
| 6,656,159 B2 | 12/2003 | Flaherty |
| 6,692,457 B2 | 2/2004 | Flaherty |
| 6,699,218 B2 | 3/2004 | Flaherty et al. |
| 6,723,072 B2 | 4/2004 | Flaherty et al. |
| 6,736,796 B2 | 5/2004 | Shekalim |
| 6,749,587 B2 | 6/2004 | Flaherty |
| 6,752,787 B1 | 6/2004 | Causey, III et al. |
| 6,768,425 B2 | 7/2004 | Fleherty et al. |
| 6,800,071 B1 | 10/2004 | McConnell et al. |
| 6,817,990 B2 | 11/2004 | Yap et al. |
| 6,830,558 B2 | 12/2004 | Flaherty et al. |
| 6,852,104 B2 | 2/2005 | Blomquist |
| 6,902,207 B2 | 6/2005 | Lickliter |
| 6,937,955 B2 | 8/2005 | Barnes |
| 6,939,324 B2 | 9/2005 | Gonnelli et al. |
| 6,997,907 B2 | 2/2006 | Safabash et al. |
| 7,029,455 B2 | 4/2006 | Flaherty et al. |
| 7,033,338 B2 | 4/2006 | Vilks et al. |
| 7,063,684 B2 | 6/2006 | Moberg |
| 7,137,964 B2 | 11/2006 | Flaherty |
| 7,179,226 B2 | 2/2007 | Crothall et al. |
| 7,193,521 B2 | 3/2007 | Moberg et al. |
| 7,207,974 B2 | 4/2007 | Safabash et al. |
| 7,214,207 B2 | 5/2007 | Lynch et al. |
| 7,250,037 B2 | 7/2007 | Shermer et al. |
| 7,303,543 B1 | 12/2007 | Maule et al. |
| 7,306,578 B2 | 12/2007 | Gray et al. |
| 7,311,693 B2 | 12/2007 | Shekalim |
| 7,318,816 B2 | 1/2008 | Bobroff et al. |
| 7,329,239 B2 | 2/2008 | Safabash et al. |
| 7,390,314 B2 | 6/2008 | Stutz, Jr. et al. |
| 7,455,663 B2 | 11/2008 | Bikovsky |
| 7,481,792 B2 | 1/2009 | Gonnelli et al. |
| 7,510,544 B2 | 3/2009 | Vilks et al. |
| 7,534,226 B2 | 5/2009 | Mernoe et al. |
| 7,569,050 B2 | 8/2009 | Moberg et al. |
| 7,621,893 B2 | 11/2009 | Moberg et al. |
| 7,632,247 B2 | 12/2009 | Adams |
| 7,641,628 B2 | 1/2010 | Daoud et al. |
| 7,641,649 B2 | 1/2010 | Moberg et al. |
| 7,644,986 B2 | 1/2010 | Berger et al. |
| 7,713,258 B2 | 5/2010 | Adams et al. |
| 7,713,262 B2 | 5/2010 | Adams et al. |
| 7,726,955 B2 | 6/2010 | Ryser et al. |
| 7,732,939 B2 | 6/2010 | Fuller et al. |
| 7,794,434 B2 | 9/2010 | Mounce et al. |
| 7,806,868 B2 | 10/2010 | De Polo et al. |
| 8,282,366 B2 | 10/2012 | Hilber et al. |
| 8,382,700 B2 | 2/2013 | Straessler et al. |
| 8,414,532 B2 | 4/2013 | Brandt et al. |
| 8,430,849 B2 | 4/2013 | Smith et al. |
| 8,448,523 B2 | 5/2013 | Richter |
| 8,465,460 B2 | 6/2013 | Yodfat et al. |
| 8,568,361 B2 | 10/2013 | Yodfat et al. |
| 8,777,901 B2 | 7/2014 | Smith et al. |
| 8,905,972 B2 | 12/2014 | Smith et al. |
| 8,915,879 B2 | 12/2014 | Smith et al. |
| 8,957,674 B2 | 2/2015 | Genoud et al. |
| 8,998,858 B2 | 4/2015 | Chong et al. |
| 9,114,208 B2 | 8/2015 | Smith et al. |
| 9,216,249 B2 | 12/2015 | Smith et al. |
| 9,222,470 B2 | 12/2015 | Genoud et al. |
| 9,302,285 B2 | 4/2016 | Marbet et al. |
| 9,308,320 B2 | 4/2016 | Smith et al. |
| 9,320,849 B2 | 4/2016 | Smith et al. |
| 9,381,300 B2 | 7/2016 | Smith et al. |
| 9,498,573 B2 | 11/2016 | Smith et al. |
| 9,750,875 B2 | 9/2017 | Smith et al. |
| 9,839,747 B2 | 12/2017 | Smith et al. |
| 10,029,045 B2 | 7/2018 | Smith et al. |
| 10,272,196 B2 | 4/2019 | Smith et al. |
| 10,342,918 B2 | 7/2019 | Politis et al. |
| 10,398,853 B2 | 9/2019 | Huwiler et al. |
| 10,737,016 B2 * | 8/2020 | Smith .............. A61M 5/31513 |
| 2001/0034502 A1 | 10/2001 | Moberg et al. |
| 2001/0041869 A1 | 11/2001 | Causey, III et al. |
| 2001/0053887 A1 | 12/2001 | Douglas et al. |
| 2002/0040208 A1 | 4/2002 | Flaherty et al. |
| 2002/0077598 A1 | 6/2002 | Yap et al. |
| 2002/0091358 A1 | 7/2002 | Klitmose |
| 2002/0123740 A1 | 9/2002 | Flaherty et al. |
| 2002/0151855 A1 | 10/2002 | Douglas et al. |
| 2002/0173748 A1 | 11/2002 | McConnell et al. |
| 2002/0173769 A1 | 11/2002 | Gray et al. |
| 2002/0183616 A1 | 12/2002 | Toews et al. |
| 2003/0040700 A1 | 2/2003 | Hickle et al. |
| 2003/0055380 A1 | 3/2003 | Flaherty |
| 2003/0073952 A1 | 4/2003 | Flaherty et al. |
| 2003/0100863 A1 | 5/2003 | Shekalim |
| 2003/0125672 A1 | 7/2003 | Adair et al. |
| 2003/0135159 A1 | 7/2003 | Daily et al. |
| 2003/0161744 A1 | 8/2003 | Vilks et al. |
| 2003/0163088 A1 | 8/2003 | Blomqusit |
| 2003/0163090 A1 | 8/2003 | Blomquist et al. |
| 2003/0163223 A1 | 8/2003 | Blomquist |
| 2003/0167036 A1 | 9/2003 | Flaherty |
| 2003/0167039 A1 | 9/2003 | Moberg |
| 2003/0199085 A1 | 10/2003 | Berger et al. |
| 2003/0199824 A1 | 10/2003 | Mahoney et al. |
| 2003/0199825 A1 | 10/2003 | Flaherty |

(56) References Cited

U.S. PATENT DOCUMENTS

| | | |
|---|---|---|
| 2003/0216683 A1 | 11/2003 | Shekalim |
| 2003/0233069 A1 | 12/2003 | Gillespie, Jr. et al. |
| 2004/0003493 A1 | 1/2004 | Adair et al. |
| 2004/0078028 A1 | 4/2004 | Flaherty et al. |
| 2004/0085215 A1 | 5/2004 | Moberg et al. |
| 2004/0092865 A1 | 5/2004 | Flaherty |
| 2004/0092873 A1 | 5/2004 | Moberg |
| 2004/0092878 A1 | 5/2004 | Flaherty |
| 2004/0127844 A1 | 7/2004 | Flaherty |
| 2004/0133166 A1 | 7/2004 | Moberg et al. |
| 2004/0138612 A1 | 7/2004 | Shermer et al. |
| 2004/0153032 A1 | 8/2004 | Garribotto et al. |
| 2004/0158207 A1 | 8/2004 | Hunn et al. |
| 2004/0176727 A1 | 9/2004 | Shekalim |
| 2004/0220551 A1 | 11/2004 | Flaherty et al. |
| 2004/0231667 A1 | 11/2004 | Horton et al. |
| 2004/0235446 A1 | 11/2004 | Flaherty et al. |
| 2004/0243065 A1 | 12/2004 | McConnell et al. |
| 2004/0254533 A1 | 12/2004 | Schriver et al. |
| 2005/0020980 A1 | 1/2005 | Inoue et al. |
| 2005/0021000 A1 | 1/2005 | Adair et al. |
| 2005/0021005 A1 | 1/2005 | Flaherty et al. |
| 2005/0022274 A1 | 1/2005 | Campbell et al. |
| 2005/0065472 A1 | 3/2005 | Cindrich et al. |
| 2005/0090808 A1 | 4/2005 | Malave et al. |
| 2005/0148938 A1 | 7/2005 | Blomquist |
| 2005/0171476 A1 | 8/2005 | Judson et al. |
| 2005/0182366 A1 | 8/2005 | Vogt et al. |
| 2005/0197626 A1 | 9/2005 | Moberg et al. |
| 2005/0209804 A1 | 9/2005 | Basso et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Dilanni et al. |
| 2006/0074381 A1 | 4/2006 | Malave et al. |
| 2006/0095014 A1 | 5/2006 | Ethelfeld |
| 2006/0178633 A1 | 8/2006 | Garibotto |
| 2006/0184154 A1 | 8/2006 | Moberg et al. |
| 2006/0189939 A1 | 8/2006 | Gonnelli et al. |
| 2006/0200112 A1 | 9/2006 | Paul |
| 2006/0201121 A1 | 9/2006 | Straka et al. |
| 2006/0206054 A1 | 9/2006 | Shekalim |
| 2006/0282290 A1 | 12/2006 | Flaherty et al. |
| 2007/0021733 A1 | 1/2007 | Hansen et al. |
| 2007/0049870 A1 | 3/2007 | Gray et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0100283 A1 | 5/2007 | Causey, III et al. |
| 2007/0118405 A1 | 5/2007 | Campbell et al. |
| 2007/0123819 A1 | 5/2007 | Mernoe et al. |
| 2007/0149861 A1 | 6/2007 | Crothall et al. |
| 2007/0149862 A1 | 6/2007 | Crothall et al. |
| 2007/0149926 A1 | 6/2007 | Moberg et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2007/0191772 A1 | 8/2007 | Wojcik |
| 2007/0204603 A1 | 9/2007 | Jacobs et al. |
| 2007/0219480 A1 | 9/2007 | Kamen et al. |
| 2007/0228071 A1 | 10/2007 | Kamen et al. |
| 2007/0252546 A1 | 11/2007 | Peterson |
| 2007/0276329 A1 | 11/2007 | Mernoe |
| 2007/0282269 A1 | 12/2007 | Carter et al. |
| 2007/0287960 A1 | 12/2007 | Adams et al. |
| 2007/0293826 A1 | 12/2007 | Wall et al. |
| 2007/0299397 A1 | 12/2007 | Alferness et al. |
| 2007/0299398 A1 | 12/2007 | Alferness et al. |
| 2007/0299399 A1 | 12/2007 | Alferness et al. |
| 2007/0299400 A1 | 12/2007 | Alferness et al. |
| 2007/0299401 A1 | 12/2007 | Alferness et al. |
| 2007/0299405 A1 | 12/2007 | Kaufmann et al. |
| 2007/0299408 A1 | 12/2007 | Alferness et al. |
| 2008/0021395 A1 | 1/2008 | Yodfat et al. |
| 2008/0027296 A1 | 1/2008 | Hadvary et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051738 A1 | 2/2008 | Griffin |
| 2008/0058718 A1 | 3/2008 | Adams et al. |
| 2008/0077081 A1 | 3/2008 | Mounce et al. |
| 2008/0097318 A1 | 4/2008 | Adams |
| 2008/0097324 A1 | 4/2008 | Adams et al. |
| 2008/0097381 A1 | 4/2008 | Moberg et al. |
| 2008/0119790 A1 | 5/2008 | Hawkins et al. |
| 2008/0132842 A1 | 6/2008 | Flaherty |
| 2008/0167620 A1 | 7/2008 | Adams et al. |
| 2008/0213956 A1 | 9/2008 | Black et al. |
| 2008/0215006 A1 | 9/2008 | Thorkild |
| 2008/0215015 A1 | 9/2008 | Cindrich et al. |
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0269687 A1 | 10/2008 | Chong et al. |
| 2008/0272963 A1 | 11/2008 | Chang et al. |
| 2008/0281270 A1 | 11/2008 | Cross et al. |
| 2008/0294094 A1 | 11/2008 | Mhatre et al. |
| 2008/0294142 A1 | 11/2008 | Patel et al. |
| 2008/0312512 A1 | 12/2008 | Brukalo et al. |
| 2008/0312584 A1 | 12/2008 | Montgomery et al. |
| 2008/0312585 A1 | 12/2008 | Brukalo et al. |
| 2008/0319416 A1 | 12/2008 | Yodfat et al. |
| 2009/0006129 A1 | 1/2009 | Thukral et al. |
| 2009/0030382 A1 | 1/2009 | Brandt et al. |
| 2009/0048563 A1 | 2/2009 | Ethelfeld et al. |
| 2009/0048578 A1 | 2/2009 | Adams et al. |
| 2009/0054866 A1 | 2/2009 | Teisen-Simony et al. |
| 2009/0062747 A1 | 3/2009 | Saul |
| 2009/0062768 A1 | 3/2009 | Saul |
| 2009/0067989 A1 | 3/2009 | Estes et al. |
| 2009/0069784 A1 | 3/2009 | Estes et al. |
| 2009/0069787 A1 | 3/2009 | Estes et al. |
| 2009/0076451 A1 | 3/2009 | Teisen-Simony et al. |
| 2009/0076453 A1 | 3/2009 | Mejhede et al. |
| 2009/0088682 A1 | 4/2009 | Cross et al. |
| 2009/0088689 A1 | 4/2009 | Carter |
| 2009/0088690 A1 | 4/2009 | Carter et al. |
| 2009/0088691 A1 | 4/2009 | Carter et al. |
| 2009/0088692 A1 | 4/2009 | Adams et al. |
| 2009/0088693 A1 | 4/2009 | Carter |
| 2009/0088694 A1 | 4/2009 | Carter et al. |
| 2009/0099521 A1 | 4/2009 | Gravesen et al. |
| 2009/0099523 A1 | 4/2009 | Grant et al. |
| 2009/0131860 A1 | 5/2009 | Nielsen |
| 2009/0143735 A1 | 6/2009 | De Polo et al. |
| 2009/0156989 A1 | 6/2009 | Carter et al. |
| 2009/0163865 A1 | 6/2009 | Hines et al. |
| 2009/0163866 A1 | 6/2009 | Hines et al. |
| 2009/0166978 A1* | 7/2009 | Hoffmann ......... A61M 5/31513 277/437 |
| 2009/0182277 A1 | 7/2009 | Carter |
| 2009/0192471 A1 | 7/2009 | Carter et al. |
| 2009/0198186 A1 | 8/2009 | Mernoe et al. |
| 2009/0198215 A1 | 8/2009 | Chong et al. |
| 2009/0221971 A1 | 9/2009 | Mejlhede et al. |
| 2009/0240240 A1 | 9/2009 | Hines et al. |
| 2009/0254037 A1 | 10/2009 | Bryant, Jr. et al. |
| 2009/0254041 A1 | 10/2009 | Krag et al. |
| 2009/0259176 A1 | 10/2009 | Yairi |
| 2009/0320569 A1 | 12/2009 | Haslem et al. |
| 2009/0326453 A1 | 12/2009 | Adams et al. |
| 2009/0326454 A1 | 12/2009 | Cross et al. |
| 2009/0326455 A1 | 12/2009 | Carter |
| 2009/0326456 A1 | 12/2009 | Cross et al. |
| 2009/0326472 A1 | 12/2009 | Carter et al. |
| 2010/0031424 A1 | 2/2010 | Sharpe et al. |
| 2010/0049128 A1 | 2/2010 | McKenzie et al. |
| 2010/0069848 A1 | 3/2010 | Alferness et al. |
| 2010/0100056 A1 | 4/2010 | Cawthon et al. |
| 2010/0137695 A1 | 6/2010 | Yodfat et al. |
| 2010/0198060 A1 | 8/2010 | Fago et al. |

(56) References Cited

U.S. PATENT DOCUMENTS

| | | |
|---|---|---|
| 2010/0217105 A1 | 8/2010 | Yodfat et al. |
| 2010/0241063 A1 | 9/2010 | Straessler et al. |
| 2010/0262078 A1 | 10/2010 | Blomquist |
| 2011/0034883 A1 | 2/2011 | Gyrn et al. |
| 2011/0144586 A1 | 6/2011 | Michaud et al. |
| 2011/0144615 A1 | 6/2011 | Haenggi et al. |
| 2011/0196337 A1 | 8/2011 | Brandt et al. |
| 2011/0224603 A1 | 9/2011 | Richter |
| 2011/0238015 A1 | 9/2011 | Matusch |
| 2012/0022354 A1 | 1/2012 | Beyer et al. |
| 2012/0022452 A1 | 1/2012 | Welsch et al. |
| 2012/0046651 A1 | 2/2012 | Beyer et al. |
| 2012/0053522 A1 | 3/2012 | Yodfat et al. |
| 2012/0078170 A1 | 3/2012 | Smith et al. |
| 2012/0078181 A1 | 3/2012 | Smith et al. |
| 2012/0078182 A1 | 3/2012 | Smith et al. |
| 2012/0078183 A1 | 3/2012 | Smith et al. |
| 2012/0078184 A1 | 3/2012 | Smith et al. |
| 2012/0078185 A1 | 3/2012 | Smith et al. |
| 2012/0078216 A1 | 3/2012 | Smith et al. |
| 2012/0078217 A1 | 3/2012 | Smith et al. |
| 2012/0078222 A1 | 3/2012 | Smith et al. |
| 2012/0078285 A1 | 3/2012 | Griffin |
| 2012/0116311 A1 | 5/2012 | Bruggemann et al. |
| 2012/0184907 A1 | 7/2012 | Smith et al. |
| 2012/0184909 A1 | 7/2012 | Gyrn |
| 2012/0191043 A1 | 7/2012 | Yodfat et al. |
| 2012/0215163 A1 | 8/2012 | Hanson et al. |
| 2012/0245515 A1 | 9/2012 | Calasso et al. |
| 2012/0302844 A1 | 11/2012 | Schnidrig et al. |
| 2013/0138078 A1 | 5/2013 | Smith et al. |
| 2013/0237781 A1 | 9/2013 | Gyrn |
| 2013/0310801 A1 | 11/2013 | Yodfat et al. |
| 2014/0228802 A1* | 8/2014 | Mackey ............ A61M 5/14546 604/151 |
| 2014/0231549 A1 | 8/2014 | Thiemer et al. |
| 2014/0296786 A1 | 10/2014 | Servansky et al. |
| 2015/0011939 A1 | 1/2015 | Marbet et al. |
| 2015/0073386 A1 | 3/2015 | Smith et al. |
| 2015/0126934 A1 | 5/2015 | Chong et al. |
| 2015/0133855 A1 | 5/2015 | Smith et al. |
| 2016/0030663 A1 | 2/2016 | Adaniya et al. |
| 2016/0058474 A1 | 3/2016 | Peterson et al. |
| 2016/0089491 A1 | 3/2016 | Smith |
| 2016/0184512 A1 | 6/2016 | Marbet et al. |
| 2016/0235913 A1 | 8/2016 | Smith et al. |
| 2017/0232191 A1 | 8/2017 | Smith et al. |
| 2018/0185572 A1 | 7/2018 | Smith et al. |
| 2018/0318502 A1 | 11/2018 | Smith et al. |
| 2019/0015585 A1 | 1/2019 | Smith |
| 2019/0076599 A1 | 3/2019 | Smith |
| 2019/0321543 A1 | 10/2019 | Smith et al. |
| 2020/0353165 A1 | 11/2020 | Smith et al. |

FOREIGN PATENT DOCUMENTS

| | | |
|---|---|---|
| CA | 2632995 A1 | 7/2007 |
| CA | 2659616 | 2/2008 |
| CA | 2921304 | 2/2011 |
| CA | 2842951 | 7/2011 |
| CH | 688224 A5 | 6/1997 |
| CN | 101574550 A | 11/2009 |
| CN | 101745163 A | 6/2010 |
| EP | 2324872 A2 | 5/2011 |
| JP | 59127595 A | 7/1984 |
| JP | 01298998 A | 12/1989 |
| JP | 08168297 A | 6/1996 |
| JP | 2002078386 A | 3/2002 |
| JP | 2008168297 A | 7/2008 |
| JP | 2009030311 A | 2/2009 |
| JP | 2015521948 A | 8/2015 |
| RU | 437871 A1 | 7/1974 |
| WO | 198503007 A1 | 7/1985 |
| WO | 9858693 | 12/1998 |
| WO | 9948546 A1 | 9/1999 |
| WO | 1999048546 | 9/1999 |
| WO | 0025844 A1 | 5/2000 |
| WO | 0170307 A1 | 9/2001 |
| WO | 0220073 A2 | 3/2002 |
| WO | 0228455 A1 | 4/2002 |
| WO | 02028455 A1 | 4/2002 |
| WO | 0249509 A2 | 6/2002 |
| WO | 02049509 A2 | 6/2002 |
| WO | 02094352 A2 | 11/2002 |
| WO | 03045302 A2 | 6/2003 |
| WO | 03074121 A1 | 9/2003 |
| WO | 2004091692 A2 | 10/2004 |
| WO | 2004098390 A2 | 11/2004 |
| WO | 2005018703 A2 | 3/2005 |
| WO | 2005018705 A2 | 3/2005 |
| WO | 2005037350 A2 | 4/2005 |
| WO | 2005046756 A2 | 5/2005 |
| WO | 2005072794 A2 | 8/2005 |
| WO | 2005072795 A2 | 8/2005 |
| WO | 2006032689 A1 | 3/2006 |
| WO | 2006032692 A1 | 3/2006 |
| WO | 2006061354 A1 | 6/2006 |
| WO | 2006104806 A2 | 10/2006 |
| WO | 2006108809 A1 | 10/2006 |
| WO | 2007038059 A1 | 4/2007 |
| WO | 2007038060 A2 | 4/2007 |
| WO | 2007038091 A2 | 4/2007 |
| WO | 2007094833 A1 | 8/2007 |
| WO | 2007140631 A1 | 12/2007 |
| WO | 2007142867 A2 | 12/2007 |
| WO | 2007142890 A2 | 12/2007 |
| WO | 2008040762 A1 | 4/2008 |
| WO | 2008063429 A2 | 5/2008 |
| WO | 2008078318 A2 | 7/2008 |
| WO | 2008082126 A | 7/2008 |
| WO | 2008103175 A1 | 8/2008 |
| WO | 2008122983 A1 | 10/2008 |
| WO | 2008139458 A2 | 11/2008 |
| WO | 2008139459 A1 | 11/2008 |
| WO | 2008139460 A2 | 11/2008 |
| WO | 2009016635 A2 | 2/2009 |
| WO | 2009016636 A2 | 2/2009 |
| WO | 2009016637 A2 | 2/2009 |
| WO | 2009045776 A2 | 4/2009 |
| WO | 2009045779 A2 | 4/2009 |
| WO | 2009045781 A2 | 4/2009 |
| WO | 2009045784 A2 | 4/2009 |
| WO | 2009045785 A2 | 4/2009 |
| WO | 2009066288 A1 | 5/2009 |
| WO | 2009079528 A1 | 6/2009 |
| WO | 2009081399 A1 | 7/2009 |
| WO | 2009088956 A2 | 7/2009 |
| WO | 2009097292 A2 | 8/2009 |
| WO | 2009101130 A1 | 8/2009 |
| WO | 2009113060 A2 | 9/2009 |
| WO | 2009113075 A1 | 9/2009 |
| WO | 2009116045 A1 | 9/2009 |
| WO | 2009125398 A2 | 10/2009 |
| WO | 2009133557 A2 | 11/2009 |
| WO | 2009146080 A1 | 12/2009 |
| WO | 2009158651 A2 | 12/2009 |
| WO | 2010022069 A2 | 2/2010 |
| WO | 2010026580 A2 | 3/2010 |
| WO | 2010029054 A1 | 3/2010 |
| WO | 2010029551 A2 | 3/2010 |
| WO | 2010031424 A1 | 3/2010 |
| WO | 2010051369 A1 | 5/2010 |
| WO | 2011022250 A2 | 2/2011 |
| WO | 2011146166 A1 | 11/2011 |
| WO | 2012040528 A1 | 3/2012 |
| WO | 2012103428 A2 | 8/2012 |
| WO | 2014011879 A2 | 1/2014 |
| WO | 2014116274 A | 7/2014 |
| WO | 2016133789 A2 | 8/2016 |

(56) References Cited

FOREIGN PATENT DOCUMENTS

| WO | 2017135936 A1 | 8/2017 |
| WO | 2017139723 A1 | 8/2017 |

OTHER PUBLICATIONS

Australian Application 2019284140 Examination Report No. 2; dated Oct. 7, 2020; 4 pages; (MD50015AUD3).
JP Patent Application No. 2018-542219 Notice of Reasons for Refusal (translated) dated Dec. 1, 2020, 6 pages (MD50018JP).
CN Application No. 201780023000.5 First Office Action dated Feb. 3, 2021, Translation, 8 pages.
Alaris (Carefusion, Alaris SE Pump—Directions for Use, 2011), 52 pages.
Animas Corp., "OneTouch Ping Owner's Booklet," Jul. 2008, 254 pages.
Carefusion, Alaris SE Pump Directions for Use (2011), 52 pages.
English language translation of Office Action dated May 11, 2016 in JP App. Ser. No. 2013-530335.
Extended European Search Report; Application No. 20166121.2; dated Jul. 10, 2020; 12 pages.
Extended European Search Report; Application No. 19210609.4; dated Jun. 23, 2020; 5 pages. (MD50019EPD).
Garg et al. "U-500 insulin: why, when and how to use in clinical practice", Diabetes/Metabolism Research and Reviews, vol. 23, Is. 4, 265-268.
Gnanalingham et al., "Accuracy and repoducibility of low dose insulin administration using pen-injectors and syringes," Arch Dis Child 1998; 79; 59-62.
IN Application No. 3198/DELNP/2013 Examination Report dated Nov. 22, 2019, 7 pages (MD50015IN).
International Application No. PCT/IB2018/055313 International Search Report and Written Opinion dated Dec. 7, 2018, 11 pages (MD50026PCT).
International Preliminary Report on Patentability for International Application No. PCT/US2011/052867, International Filing Date Sep. 23, 2011, dated Feb. 7, 2019, 11 pages.
International Preliminary Report on Patentability for International Application No. PCT/US2016/016214, dated Jul. 21, 2016, 12 pages (MD50013PCT).
International Preliminary Report on Patentability for International Application No. PCT/US2017/017585, International Filing Date Feb. 12, 2017, dated Aug. 14, 2018, 8 pages.
International Search Report and Written Opinion for International Application No. PCT/US2017/017585, International Filing Date Feb. 12, 2017, dated Jul. 24, 2017, 13 pages.
International Preliminary Report on Patentability for International Application No. PCT/US2016/017622, International Filing Date Feb. 11, 2016, dated Aug. 19, 2016, 10 pages.
International Search Report for International Application No. PCT/US2011/052867, International Filing Date Sep. 23, 2011, dated Feb. 7, 2012, 5 pages.
International Search Report for International Application No. PCT/US2016/016214, International Filing Date Feb. 2, 2016, dated Aug. 16, 2018, 8 pages.
International Search Report for International Application No. PCT/US2016/017622, International Filing Date Feb. 11, 2016, dated Aug. 19, 2016, 7 pages.
International Standard IEC 60601-2-24, First Edition, Feb. 1998. Medical electrical equiptment—Part2-24: Particular requirements for the safety of infusion pumps and controllers.
Jahn et al.; "Comparative Dose Accuracy of Durable and Patch Insulin Infusion Pumps"; Journal of Diabetes Science and Technology; 7(4); pp. 1011-1020; Jul. 2013.
JP Patent Application No. 2018-147576 Notice of Reasons for Rejection dated Nov. 28, 2019, 8 pages (MD50015JPD2).
JP Patent Application No. 2018-559665 Notice of Reasons for Rejection dated Dec. 5, 2019, 5 pages (MD50013JP).
Knee et al. (A novel use of U-500 insulin for continuous subcutaneaous insulin infusion in patients with insuliin resistance, Endocrine Practice, vol. 9, No. 3, May 2003), 1 page.
Kristensen et al., "Dose accuracy and durability of a durable insulin pen before and after simulated lifetime use," Current Medical Research and Opinion, Oct. 2011; 27, No. 10: 1877-1883.
Medtronic (The MiniMed, Paradigm Real-Time, Insulin Pump and Continuous Glucose Monitor System, Insulin Pump User Guide, 2008), 262 pages.
Extended European Search Report dated Apr. 5, 2016 in EP App. Ser. No. 11827581.7; dated Apr. 5, 2016; 4 pages.
Novo Nordisk Canada, Inc., "NovoPen4 User Manual English," 2009, 30 pages.
Novo Norisk Canada, Inc. NovoPen Echo User Manual English, Sep. 2009, 34 pages.
PCT Int. Search Report and Written Opinion dated Feb. 7, 2012, in related PCT App. Ser. No. PCT/US2001/052867.
Written Opinion for International Application No. PCT/US2011/052867, International Filing Date Sep. 23, 2011, dated Feb. 7, 2012, 10 pages.
Written Opinion for International Application No. PCT/US2016/016214, dated Jul. 21, 2016, 11 pages (MD50013PCT).
Written Opinion for International Application No. PCT/US2016/017622, International Filing Date Feb. 11, 2016, dated Aug. 19, 2016, 9 pages.
European Office Action; Application No. 17706380.7-1122; dated Aug. 18, 2020; 7 pages (MD50018EP).
CN Application No. 201680083837.4; English Translation of Office Action dated Aug. 6, 2020, 11 pages (MD50013CN).

\* cited by examiner

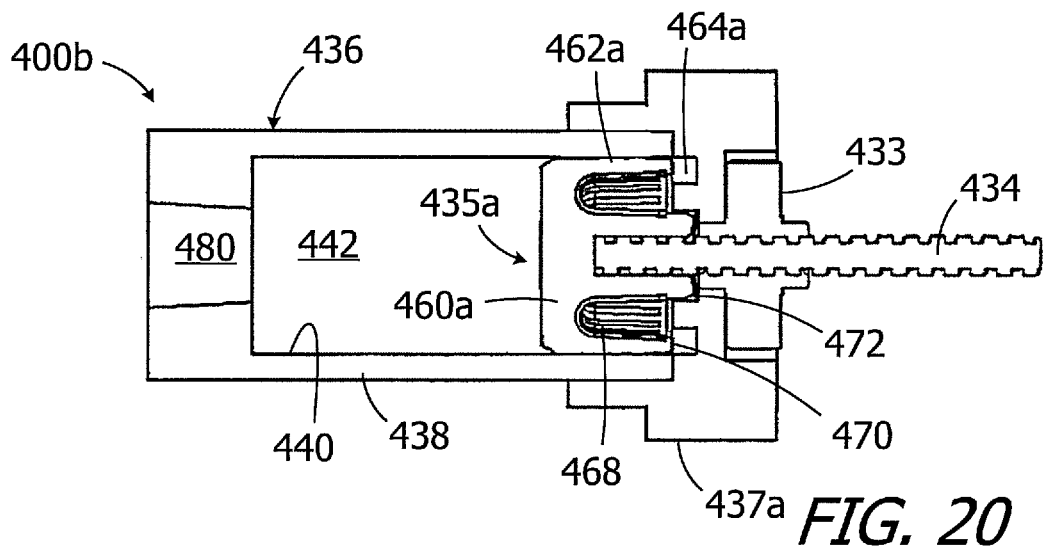
FIG. 20
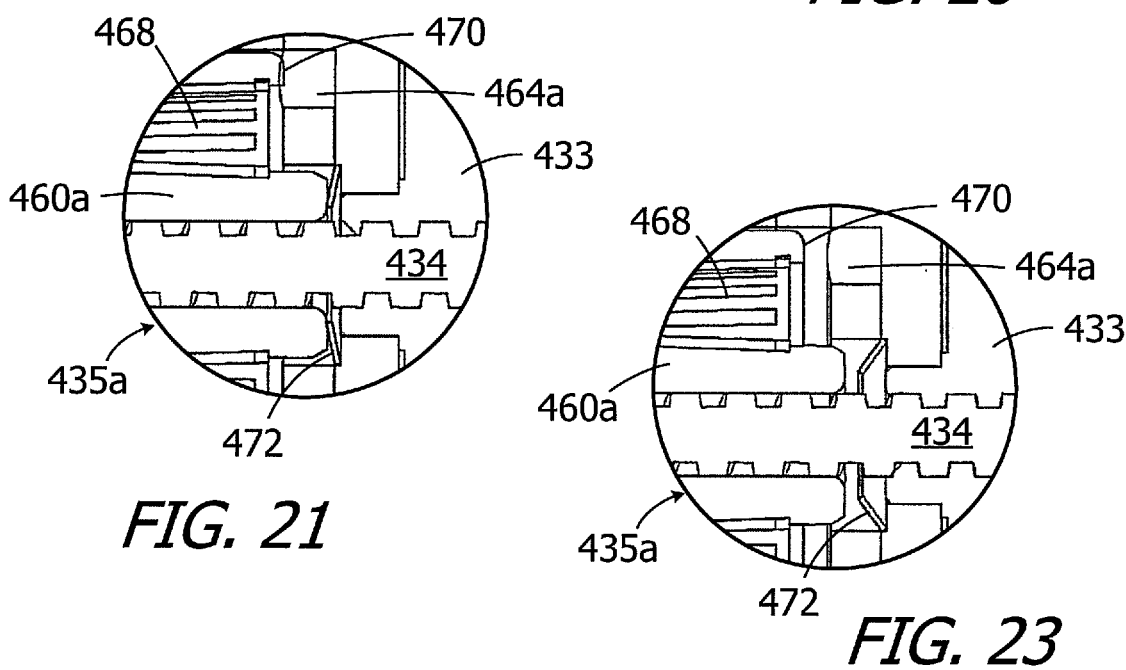
FIG. 21
FIG. 23
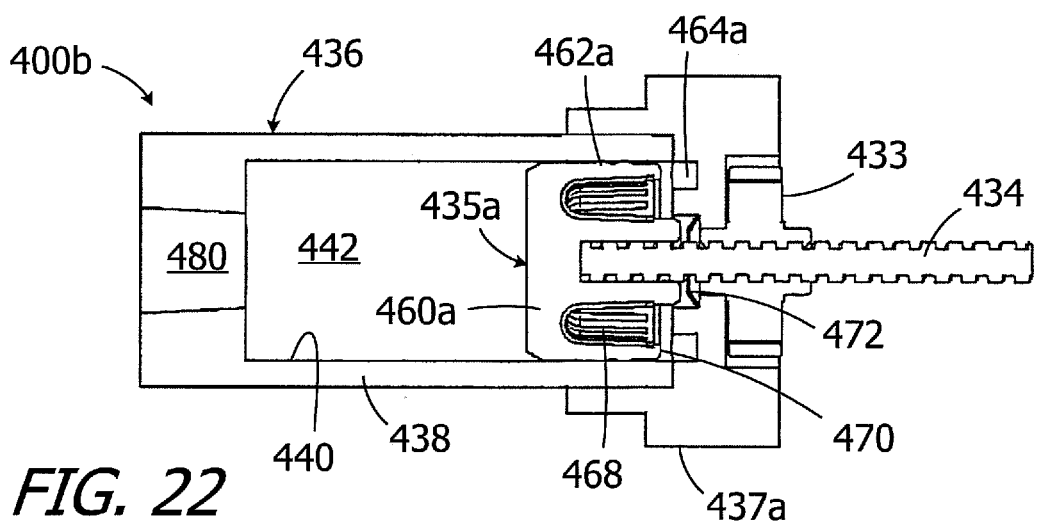
FIG. 22

AMBULATORY INFUSION PUMPS AND RESERVOIR ASSEMBLIES FOR USE WITH SAME

CROSS-REFERENCE TO RELATED APPLICATIONS

This application is a continuation of U.S. application Ser. No. 15/042,093, filed Feb. 11, 2016, which claims the benefit of and priority to U.S. Provisional Application Ser. No. 62/117,565, filed Feb. 18, 2015 and entitled "Ambulatory Infusion Pump Seals," which are incorporated herein by reference in their entirety.

BACKGROUND

1. Field

The present devices and methods relate generally to ambulatory infusion pumps and seals for those pumps.

2. Description of the Related Art

Ambulatory infusion pumps (also referred to herein simply as "infusion pumps") are relatively small, at least substantially self-contained devices that are used to introduce drugs and other infusible substances (collectively "medicament") into patients' bodies. Some infusion pumps are configured to be worn on a belt, carried in a clothing pocket, or the like. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin. Other exemplary medicaments that may be introduced by an infusion pump include, but are not limited to, drugs that treat cancers and drugs that suppress the perception of pain.

Many conventional infusion pumps have improved patient health and quality of life. Nevertheless, the present inventors have determined that conventional infusion pumps are susceptible to a wide range of improvements. By way of example, but not limitation, the present inventors have determined that it would be desirable to provide an infusion pump that is smaller, simpler, and less costly than conventional infusion pumps, while also being more accurate than conventional infusion pumps.

SUMMARY

An infusion pump reservoir assembly in accordance with at least one of the present inventions includes a medicament reservoir and a plunger that is moveable within the medicament reservoir and includes a dynamic seal. The assembly may further include a static seal. When the system begins to dispense medicament, the plunger may automatically disengage from the static seal while the dynamic seal remains in contact with the inner surface of the reservoir. The present inventions also include infusion pumps including such medicament reservoir assemblies.

A method in accordance with at least one of the present inventions includes the step of automatically disengaging a plunger from a static seal upon commencement of medicament dispensing from an infusion pump.

A method in accordance with at least one of the present inventions includes the step of reducing the energy required to begin medicament dispensing from an infusion pump that includes a plunger by providing a static seal that automatically disengages from the plunger upon commencement of medicament dispensing.

The features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments will be made with reference to the accompanying drawings.

FIG. 20 is a section view of an exemplary reservoir assembly with the plunger in the full position.

FIG. 21 is an enlarged view of a portion of a FIG. 20.

FIG. 22 is a section view of the reservoir assembly illustrated in FIG. 20 with the plunger not in the full position.

FIG. 23 is an enlarged view of a portion of FIG. 22.

DETAILED DESCRIPTION

Figure 1A:
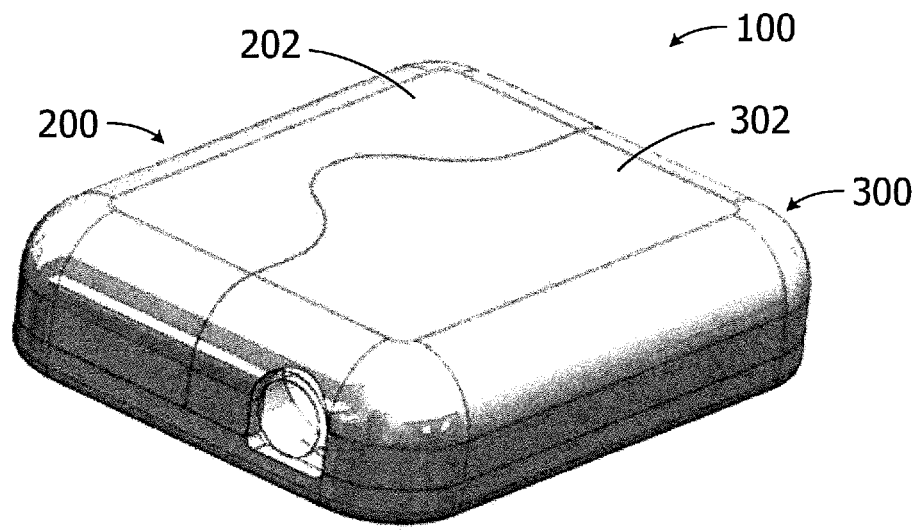
FIG. 1A is a perspective view of an exemplary infusion pump system in an assembled state.

The following is a detailed description of the best presently known modes of carrying out the inventions. This description is not to be taken in a limiting sense, but is made merely for the purpose of illustrating the general principles of the inventions.

It should also be noted here that the specification describes structures and methods that are especially well-suited for the subcutaneous delivery of very high concentration insulin (i.e., U-200 insulin and above) such as U-500 insulin as well as lower concentration insulin such as U-100 insulin. Nevertheless, it should be appreciated that the present inventions are applicable to a wide variety of infusion pumps and medicaments. By way of example, but not limitation, the inventions may employ, for fluid displacement, a reservoir with a plunger, a fluid displacement device in the form of a plunger pusher, and a drive mechanism that includes a motor, or other fluid displacement devices, regardless of the type of reservoir employed, piston pumps (e.g., electromagnet pumps), MEMS pumps, peristaltic pumps and any other suitable pumps as well as corresponding drive mechanisms. Exemplary infusion pumps that include a reservoir with a plunger, a fluid displacement device in the form of a plunger pusher, and a drive mechanism are described in U.S. patent application Ser. No. 12/890,207, filed Sep. 24, 2010, and corresponding U.S. patent publication No. 2012/0078170, both of which are incorporated by reference in their entireties, and in U.S. provisional patent application Ser. No. 62/057,273, filed Sep. 30, 2014, and corresponding U.S. patent application Ser. No. 14/869,906, filed Sep. 29, 2015, which are also incorporated by reference in their entireties. The present inventions are also applicable to medicaments such as, for example, drugs to mask pain, chemotherapy and other cancer related drugs, antibiotics, hormones, GLP-1, Glucagon, various other drugs that include large molecules and proteins that may require a high level of delivery accuracy, as well as to relatively high concentration insulin (i.e., U-200 insulin and above) such as U-500 insulin and lower concentration insulin such as U-100. Aforementioned U.S. patent publication No. 2012/0078170, U.S. provisional patent application Ser. No. 62/057,273 and U.S. patent application Ser. No. 14/869,906 each also describe patient interaction with and use of infusion pumps such as the exemplary infusion pumps described herein.

As noted above, some ambulatory infusion pumps are intended to be worn on a belt, carried in a pocket, or otherwise supported within a holder of some kind (referred to collectively as "pocket pumps"). Such infusion pumps transfer fluid from a reservoir to an infusion set by way of an elongate tube. Subcutaneous access may be obtained by way of a cannula in the infusion set. Other ambulatory infusion pumps are intended to be adhered to the skin above the delivery site (sometimes referred to as "patch pumps"). Here, the cannula or other subcutaneous access device may extend directly from the infusion device. Given these modes of use, patients typically prefer the device to be as small as possible so it is more comfortable, less obtrusive, and less visible. In addition, patients want a device that is easy and convenient to use.

Figure 1B:
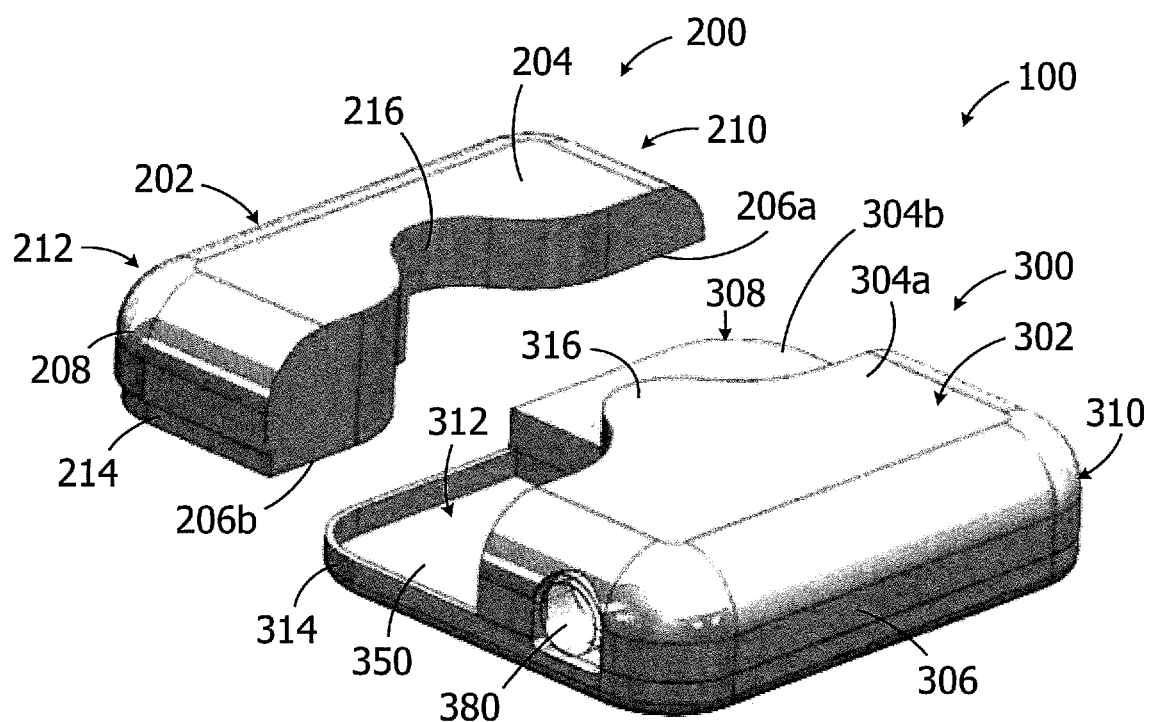
FIG. 1B is an exploded perspective view of the infusion pump system illustrated in FIG. 1A, including a durable assembly and a disposable assembly.
Figure 2:
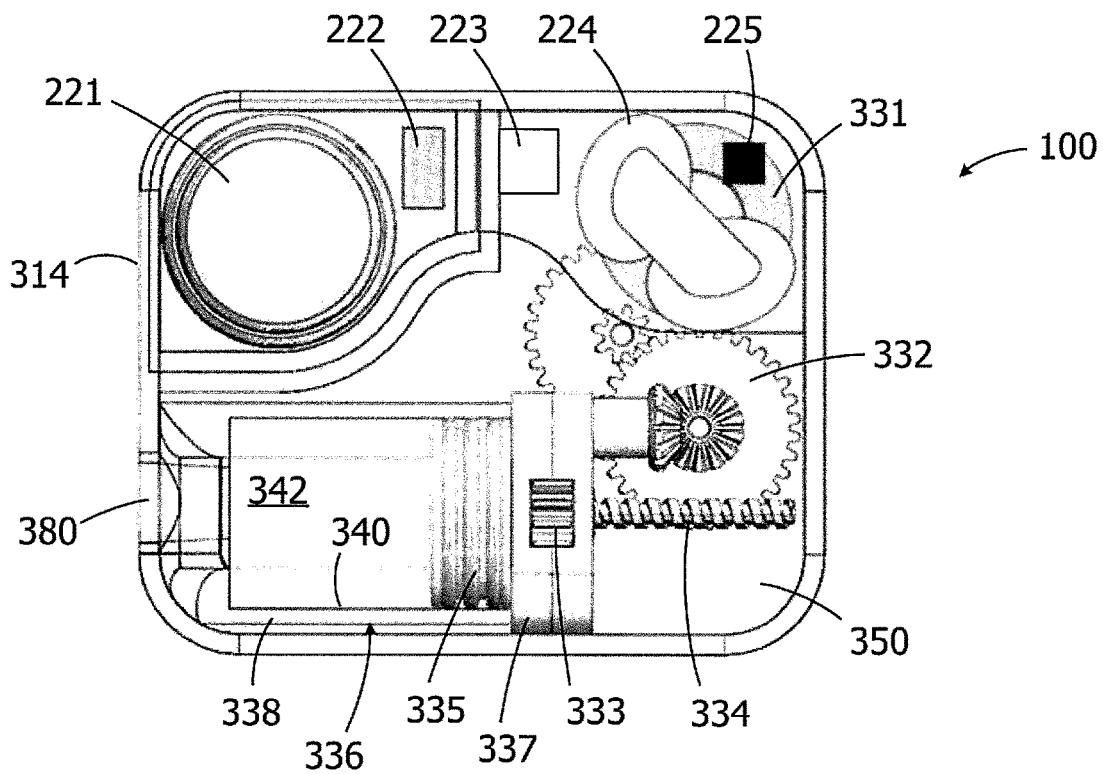
FIG. 2 is a top view of certain components of the infusion pump system illustrated in FIGS. 1A and 1B.

An exemplary ambulatory infusion system, which is generally represented by reference numeral 100 in FIGS. 1A, 1B, and 2, includes a durable assembly 200 and a disposable assembly 300. Exemplary durable assembly 200 includes a housing 202, one or more batteries or other energy supply 221, one or more capacitors or other energy storage 222, a microprocessor 223, a coil assembly 224 (which functions as a motor stator), and one or more Hall effect sensors 225. Exemplary disposable assembly 300 includes a baseplate 350 supporting components such as a magnetic motor rotor 331, a gear train 332 including lead screw drive gear 333 in a reservoir support block 337, and a lead screw 334 attached to plunger 335, which is positioned in a medicament reservoir 336 that is mounted to the reservoir support block 337. The exemplary plunger 335 includes a core and a plurality of seals on the core. A cover 302, under which some or all of the magnetic motor rotor 331, gear train 332 (with drive gear 333), lead screw 334, plunger 335, and medicament reservoir 336 are located in various embodiments, may be mounted to the baseplate 350.

The lead screw drive gear 333, lead screw 334, plunger 335, medicament reservoir 336 and reservoir support block 337 may also be referred to collectively as a "reservoir assembly." Other exemplary reservoir assemblies that may be employed in, for example, infusion system 100 are described below with reference to FIGS. 10-23.

The exemplary disposable assembly 300 may be secured to the exemplary durable assembly 200, as shown in FIGS. 1A and 2. To that end, the exemplary housing 202 includes a top wall 204, bottom walls 206a and 206b and a side wall 208 that together define a relatively thin housing portion 210 and a relatively thick housing portion 212. An indentation 214 is formed in the relatively thick portion 212. The exemplary cover 302 includes top walls 304a and 304b and a side wall 306 that together define a relatively thin cover portion 308 and a relatively thick cover portion 310. A portion of the baseplate 350 is not covered by the cover 302, thereby defining a recess 312 that is bordered by a wall 314 that extends around the baseplate (see also FIG. 4B). When the durable and disposable assemblies 200 and 300 are secured to one another in the manner illustrated in FIG. 1A, the relatively thick portion 212 of the housing 202 will reside in the recess 312 of the disposable assembly 300 (with the wall 314 in the indentation 214). The relatively thin portion 210 of the housing 202 will reside on the top wall 304b of the cover 302. The cover 302 also includes a projection 316 that mates with a recess 216 on the housing 202. Additionally, as is discussed in greater detail below, the disposable assembly 300 may be configured for different medicaments, such as different medicament concentrations, different medicament amounts, or different modes of system operation.

In other implementations, the cover 302 may be configured to cover fewer than all of the components on the baseplate 350. For example, a cover may be configured such that the magnetic motor rotor 331 and a portion of the gear train 332 are not under the cover, while the remaining components are under the cover. In still other implementations, the cover 302 may be omitted and the durable assembly 200 may be configured to cover all of the components on the baseplate 350. In yet other implementations, what is referred to in the present application as the "durable" assembly, may be disposable, resulting in a fully disposable system.

Figures 2A, 2B:
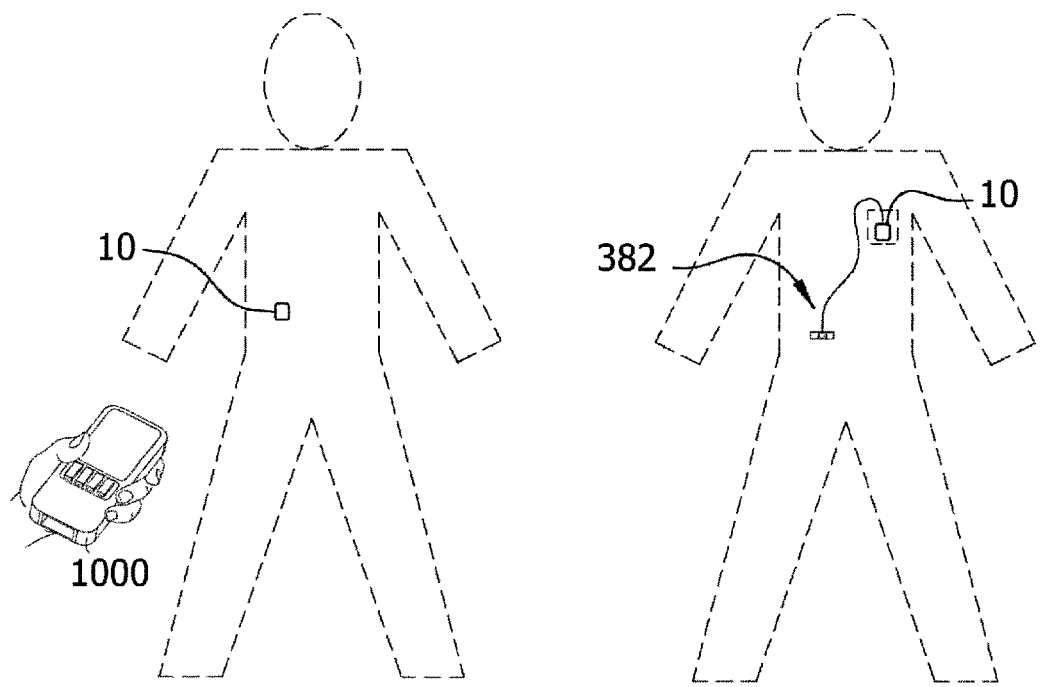
FIG. 2A is a schematic view showing a use of the infusion pump system illustrated in FIGS. 1A and 1B.
FIG. 2B is a schematic view showing another use of the infusion pump system illustrated in FIGS. 1A and 1B.

As discussed in U.S. patent publication No. 2012/0078170 described above, and in U.S. application Ser. No. 13/300,574, filed Nov. 19, 2011, and corresponding U.S. patent publication No. 2012/0184907, and in U.S. application Ser. No. 13/475,843, filed May 18, 2012, and corresponding U.S. patent publication number 2013/0138078, each of which are incorporated by reference in their entireties, ambulatory infusion systems that employ a reservoir on a baseplate may be configured for different types of use. For example, disposable assembly 300 may be adhered to the patient's skin and may be used in conjunction with a cannula (not shown) that is operatively connected to the reservoir 336 so that the system 100 may be deployed as a "patch-pump," as shown in FIG. 2A. Alternatively, as shown in FIGS. 2B, the baseplate 350 of disposable assembly 300 may be configured to operably connect the reservoir 336 to an infusion set 382 (e.g., by way of the illustrated infusion set tube and a connector 380 shown in FIGS. 1B and 2) so that the system 100 may be deployed as a "pocket pump," a "belt-worn pump" or some other wearable pump. In other words, using the same durable assembly 200, the user may configure the system for use as "pocket pump" or a "patch pump" by simply selecting the appropriate disposable assembly and attaching the disposable assembly to the durable assembly. The user may also switch from one configuration to another, by simply removing one disposable assembly and replacing it with another disposable assembly.

It should therefore be noted that the present inventions include kits that contain various combinations of disposable assemblies, where at least two of the disposable assemblies may be different. Additionally or alternatively, kits or other packages may include various disposable assembly components, such as an infusion set and/or cannula inserter. Kits may also include a durable assembly. The disposable assemblies in such kits may also include the detection/identification instrumentalities discussed below. The components of the present kits (e.g., combination of various disposable assemblies and/or components) may be stored in a common package, with individual packages for each component if necessary, and provided to the user in the common package. Other components that may be provided in such kits include, but are not limited to, inserters that are preloaded with a cannula, and cleaning swabs. A recharger may also be provided in a kit that includes a durable assembly.

In addition to disposable assembly packaging and labeling, the different disposable assemblies may include visual cues to differentiate the various disposable assemblies. For instance, disposable assemblies with different concentrations of medicament or different medicament fill volumes may use different colors for the reservoir and/or baseplate of the disposable assembly, or mechanical features that ensure disposables are only able to attach to correctly programmed durables.

It should also be noted here that, but for the issue of priming, the dispensing procedures associated with an infusion system "patch pump" configuration, which may include a durable assembly 200 and a disposable assembly 300, are substantially the same as the dispensing procedures associated with a "pocket pump" configuration, which may also include an infusion set 382 (see FIG. 2B). With a "patch pump" configuration, priming is not necessary because the volume of the associated cannula will be very small and there is a direct connection between the cannula and the medicament reservoir. Priming is, however, required to fill the infusion set tube (FIG. 2B) in a "pocket pump" configuration prior to the onset of medicament delivery. For instance, 20-30 µl may be required to fill the entire infusion set tube and, accordingly, the priming procedure may involve the rapid delivery of 10-15 IUs of U-500 insulin to the tube. The present inventors have determined that it would be advantageous to prevent users from initiating a priming procedure when the system is in the "patch pump" configuration, with a cannula positioned to deliver medicament essentially directly from the medicament reservoir to the patient, because rapidly delivering 10-15 IUs of insulin to the patient could adversely affect patient health.

To prevent such undesirable outcomes, and for user convenience in other situations involving the choice between a variety of disposable assemblies (such as disposable assemblies with reservoirs containing different medicaments, different concentrations of a medicament, and/or varying amounts of medicaments), at least some of the present disposable assemblies may be provided with a baseplate identification device and at least some of the present disposable assemblies may be provided with structure that cooperate with a baseplate identification device in such a manner that the durable assembly microprocessor/controller can make a "baseplate type" determination. Exemplary baseplate identification instrumentalities and methodologies may be as described in aforementioned U.S. patent publication Nos. 2012/0078170, 2012/0184907, and 2013/0138078. In addition, baseplate identification may be performed mechanically. For instance, a pin or rib may prevent attachment of certain disposable assemblies with certain durable assemblies. Additionally or alternative, certain durable assemblies will simply not function with certain disposable assemblies.

Alternatively, the patient or a clinician may program the system, such as via a remote control, to indicate the type of disposable assembly attached. In a manner such as this, a patient can access a variety of medicaments for use with a single durable assembly.

Once the "baseplate type" determination is made (e.g., "patch pump" disposable assembly 300 versus a "pocket pump" with infusion set 382 attached), the durable assembly will proceed in a manner, or mode of operation, that is appropriate for the attached disposable assembly. For example, if "patch pump" disposable assembly 300 is detected, the durable assembly controller will not include priming as part of the delivery process and, in some implementations, will prevent the user from manually implementing a priming procedure. If, on the other hand, a "pocket pump" disposable assembly is detected, then the delivery process may include appropriate priming of the infusion set tube.

Whether configured as a "pocket pump" or a "patch pump," the system may be configured to provide basal delivery of medicament in accordance with a delivery profile provided by a physician by way of a clinician's programming unit. For example, the system may include a program that stores a number of delivery profiles (e.g., delivery profiles associated with a 24-hour delivery cycle, delivery profiles for particular situations such as sleep or illness, and the like). Each delivery profile specifies multiple doses (or pump "operations") over time, e.g., a particular number of doses at particular times or a particular number of doses per unit time. In some implementations, a dose may be the volume associated with the minimum controllable displacement of the plunger 335. The system may also be configured to provide bolus delivery in response to an instruction from a patient remote control 1000 (FIG. 2A). A bolus instruction may come in response to a high glucose level measurement in the case of a diabetic patient, an increase in pain level in the case of a pain management patient, or some other symptom. The system may also be configured to perform other functions, such as ending medicament delivery in response to instructions from patient remote control 1000.

The present infusion pumps may be used in conjunction with a wide variety of remote controls. Such remote controls may be used to, for example, allow the user to transmit instructions to the durable assembly 200 or facilitate communication between durable assembly 200 and the user (e.g., an alarm condition message or other message concerning the conditions of system 100). An exemplary remote control 1000 (FIG. 2A) may be configured to facilitate one, some, or all of the following operations: (1) turning the remote control 1000 on or off, (2) associating (or "assigning") the remote control 1000 to the durable assembly 20, (3) obtaining status information such as medicament level, battery charge level, and/or alarm conditions, (4) silencing the durable assembly alarm, (5) selecting options that may be associated with the durable assembly alarm such as type of alarm (audible, palpable, and/or visible) and strength/volume of alarm, (6) connecting remote control 1000 to a computer to, for example, update remote control or durable assembly firmware, load and delete delivery profiles stored in the durable assembly or remote control, and otherwise reprogram the durable assembly or remote control, (7) selecting medicament options such as medicament concentrations, (8) selecting and initiating a stored medicament delivery profile, (9) increasing and decreasing medicament dose rate, and/or (10) pausing a dispensing operation. A user may pause delivery in order to remove or replace a patient applied structure (e.g., a disposable assembly), adjust for a current or anticipated changed body condition (e.g., low glucose, vigorous exercise), follow a physician's suggestion, or disconnect the durable assembly from the body for any other reason.

The exemplary remote control 1000 (FIG. 2A) may be configured to generate an indicator, based on information from a microprocessor 223 for durable assembly 200, that is indicative of, for instance, the amount of time remaining in the current dispensing program, the amount of time until the next disposable assembly replacement, etc. The indicator may be audible, visible, palpable, or combinations thereof. A time remaining indicator may be useful for a variety of reasons. For example, knowledge of the time remaining prior to next disposable assembly replacement allows the patient to determine, based at least in part on the current time of day and upcoming events (e.g., travel or sleep), whether or not it would be more convenient to replace the disposable assembly at a time prior to the end of the dispensing program.

As described above, parts of the present systems may be considered the reusable parts, while other parts may be considered the disposable parts. In the illustrated embodiments, the durable assembly 200, which may include structures such as microprocessor 223 and coil assembly 224, is reusable, while exemplary disposable assemblies 300, which may include structures such as a motor rotor 331 and reservoir 336 on a baseplate 350, are disposable.

With respect to dimensions, some embodiments of the exemplary infusion pump system 100 may have the following dimensions: length dimensions of 35 mm+/−1.0 mm, 35 mm+/−0.10 mm, or 35 mm+/−5.0 mm; width dimensions of 30 mm+/−1.0 mm, 30 mm+/−0.10 mm, or 30 mm+/−5 mm; and overall thickness or height dimensions of 8.5 mm+/−1.0 mm, 8.5 mm+/−2 mm, or 8.5 mm+/−0.10 mm. Suitable housing materials include, but are not limited to, plastic or other materials having a modulus of elasticity of 0.2-1.0 million psi.

Exemplary durable assembly microprocessors and associated circuitry; rechargeable batteries and associated battery rechargers and recharging methods; battery and recharging management; temperature sensors; and exemplary alarms and alarm conditions are described in more detail in aforementioned U.S. patent publication Nos. 2012/0078170, 2012/0184907, and 2013/0138078.

Figure 3A:
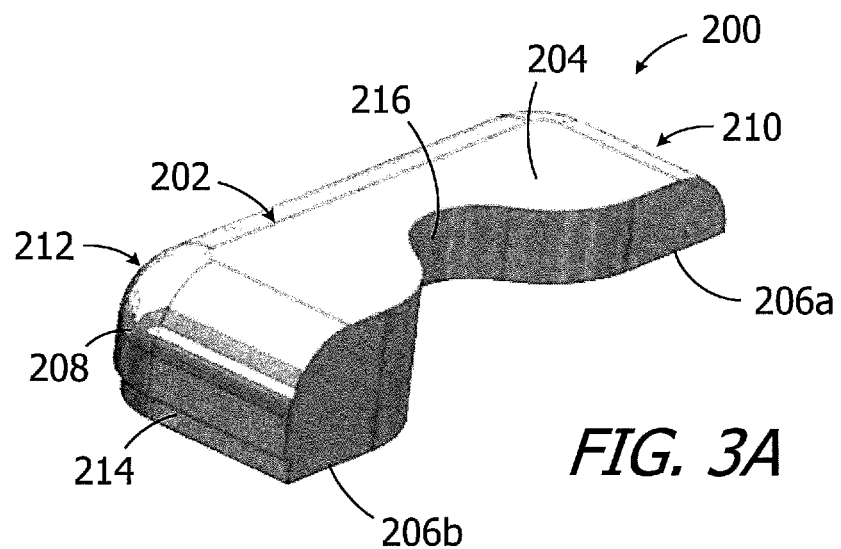
FIG. 3A is a perspective view of an exemplary durable assembly.
Figure 3B:
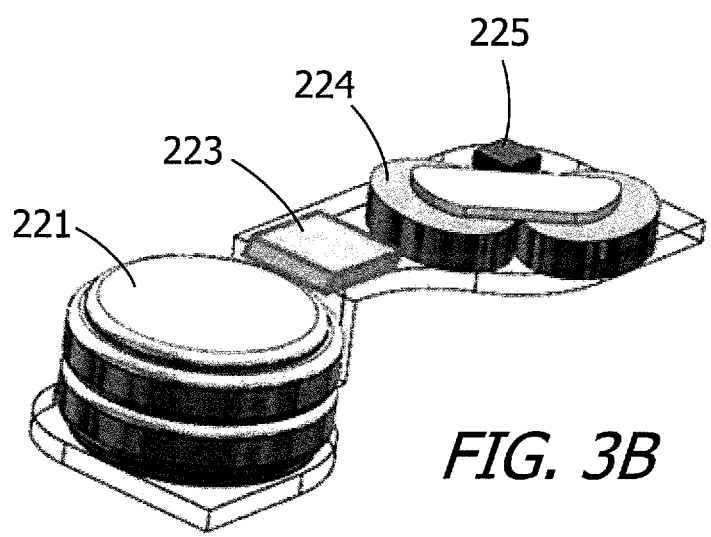
FIG. 3B is a perspective view of certain components of the durable assembly illustrated in FIG. 3A.

Turning now to FIGS. 3A and 3B, an exemplary durable assembly 200 may include a power source such as one or more batteries 221, temporary power storage such as one or more capacitors 222 (see FIGS. 2 and 5B), a controller such as microprocessor 223, a coil assembly 224, and a hall effect sensor 225. Those of skill in the art will appreciate that including the motor's coil assembly 224 and all other electronics within the durable assembly 200 reduces the cost and complexity of disposable assembly 300. In addition, the microprocessor 223 provides flexibility to include features such as user data storage, programs, programmability, adjustability, a display, buttons, wireless communication protocols, or the like to the pump 100. Durable assembly 200 may also be molded with locking features that snap onto the disposable assembly 300, but that also allow removal of the durable assembly 200 from the disposable assembly 300 either while the disposable assembly remains in place on the patient (after medicament delivery has been paused), or after the entire system has been removed from the patient.

The power source may be one or more commercially available batteries, such as a commercially available zinc-air battery or lithium polymer battery. The batteries may be selected to have sufficient capacity to operate the system for certain delivery amounts or delivery times, such as for over 400 units of delivered insulin. The optional power storage may be one or more commercially available capacitors or super-capacitors or other temporary storage device(s).

Figure 4A:
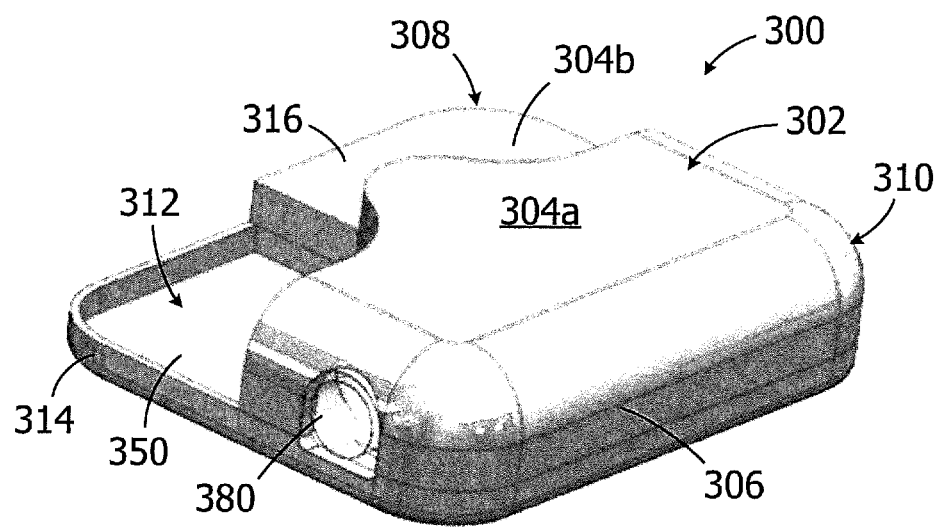
FIG. 4A is a perspective view of an exemplary disposable assembly.
Figure 4B:
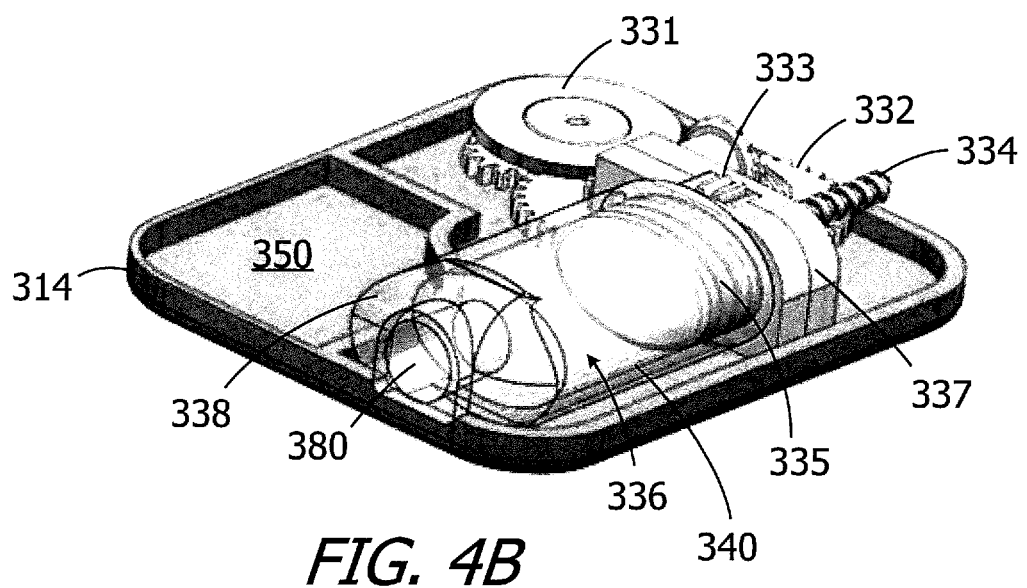
FIG. 4B is a perspective view of certain components of the disposable assembly illustrated in FIG. 4A.

Turning now to FIGS. 4A and 4B, an exemplary disposable assembly 300 may include baseplate 350 and components such as a reservoir 336, a plunger 335 within the reservoir and connected to lead screw 334, and a magnetic motor rotor 331 mechanically attached through gear train 332 to affect rotation of the lead screw drive gear 333, which causes translation of the lead screw 334 and plunger 335 within reservoir 336. The cover 302 is positioned over these components in the illustrated embodiment. The exemplary baseplate 350 includes an adhesive backing for attachment to the patient with a removable adhesive cover. The baseplate 350 may also be molded with baseplate locking features that snap onto the durable assembly 200 (such as magnets molded into the housings of each assembly), and that also allows removal of the durable assembly 200 from the disposable assembly 300.

Referring to FIGS. 2 and 4B, the exemplary reservoir 336 includes a barrel 338 with an inner surface 340 defining a fluid storage volume 342 and an oval cross-section, but other shapes (such as circular) are possible as is discussed below with reference to FIGS. 10-23. A plunger 335 with a matching cross-sectional shape fits within the barrel and carries a fluid seal such as, but not limited to, o-rings, to seal the medicament within the storage volume 342. The exemplary plunger 335 is formed from rubber and includes three o-ring seals. The reservoir 336 includes a connector 380 that may be used for filling reservoir 336, or for attaching a cannula for "patch-pump" type configurations, or for connecting (potentially via an appropriate adapter(s)) an infusion set for "pocket-pump" type configurations. The plunger 335 moves within the barrel 338 to vary the volume of medicament within the storage volume 342. Reservoir 336 may be, for instance, prefilled (or user-filled) with U-500 insulin in various volumes to suit the patient use profile. In other instances, lower concentrations of insulin, such as U-100 insulin and U-200 insulin, may be employed. A plug may be inserted in the connector 380 to maintain a sterile environment until use. The patient would remove the plug prior to use, in those instances.

Additional exemplary baseplates for use with the disposable assemblies of the present inventions, as well as exemplary cannula designs, fluidic connection between a medicament reservoir and the cannula, cooperation between the cannula and disposable assemblies (for instance, to prevent axial movement of the cannula relative to the baseplate and patient), attachment of an infusion set to the reservoir of the disposable assembly, configurations and uses of a non-delivery baseplate, arrangements and structures for attaching disposable and durable assemblies, skin adhesive designs, and various occlusion sensors, may be as described in U.S. patent application Ser. No. 12/890,207, filed Sep. 24, 2010 and corresponding U.S. patent publication number 2012/0078170, as well as aforementioned U.S. patent publication Nos. 2012/0184907 and 2013/0138078.

Figure 5A:
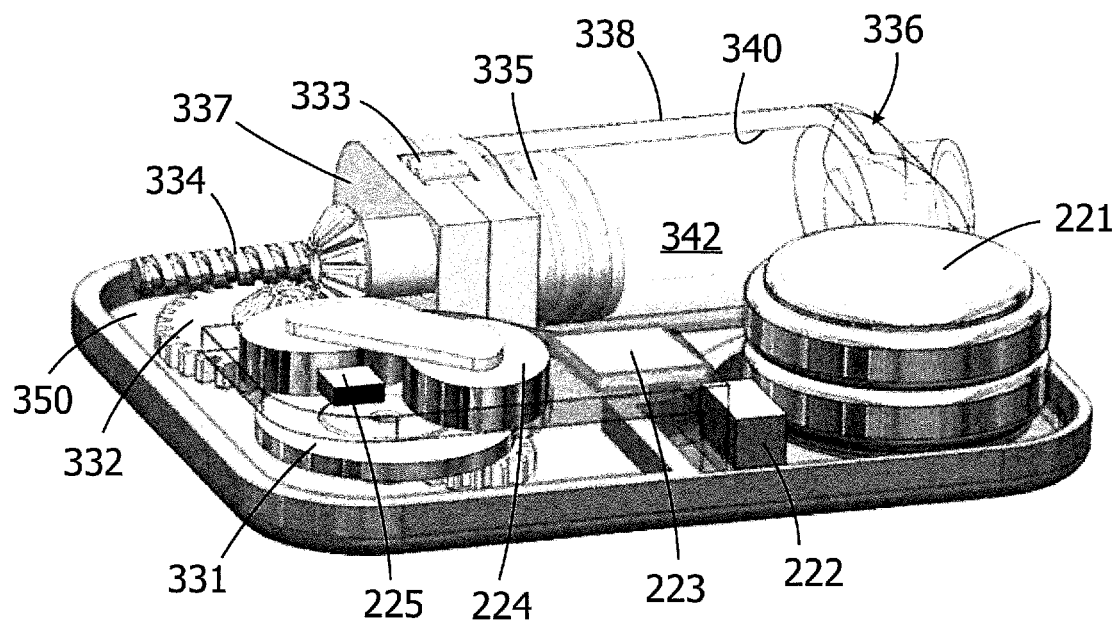
FIG. 5A is a perspective view of certain components of a durable assembly and a disposable assembly of an exemplary infusion pump system.
Figure 5B:
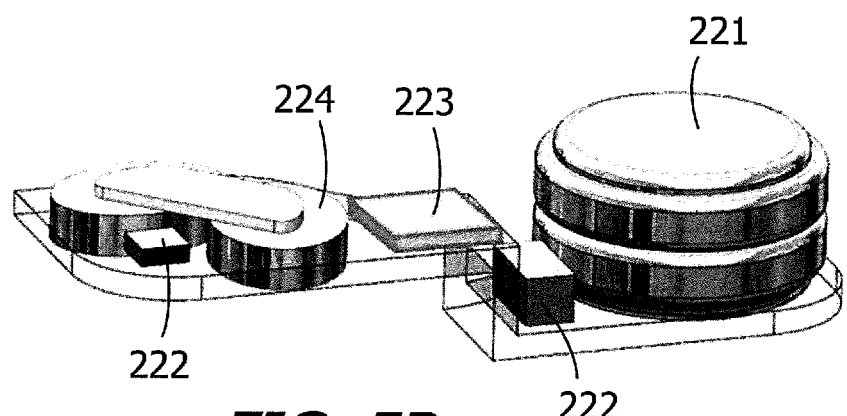
FIG. 5B is a perspective view of the components of the exemplary durable assembly illustrated in FIG. 5A.
Figure 5C:
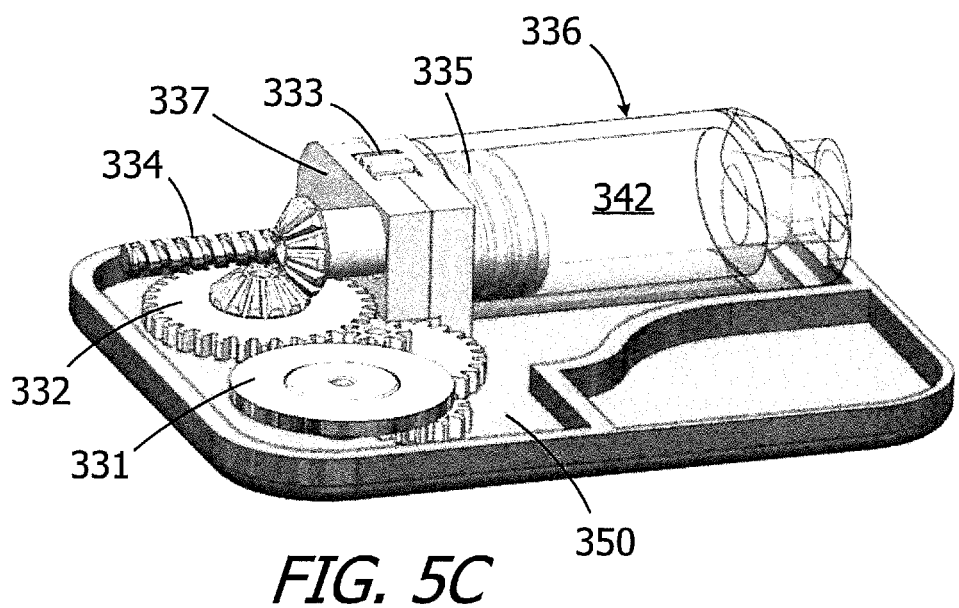
FIG. 5C is a perspective view of the components of the exemplary disposable assembly illustrated in FIG. 5A.

Turning now to FIGS. 5A-5C and the illustrated two-piece motor, the motor's coil assembly 224 (and a Hall effect sensor 225) of the durable assembly 200 are positioned above the magnetic motor rotor 331 that is part of the disposable assembly 300. An exemplary multi-pole motor rotor 331 may be disc-shaped and have a 9.8 mm outer diameter, 5.2 mm inner diameter, and 0.8 mm thickness. Another example motor rotor may have an 11 mm outer diameter, 5 mm inner diameter, and 1.2 mm thickness. Multi-pole motor rotors of this type typically cost less than 5 cents per piece, helping control the total cost of disposable assembly 200. The motor rotor 331 is also parallel to the baseplate 350, i.e., the motor rotor axis of rotation is perpendicular to the baseplate, in the illustrated embodiment. The microprocessor 223 directs rotation of motor rotor 331 by sequentially energizing the coils of motor coil assembly 224 to create an electromagnetic torque coupling between the motor coil assembly 224 and the motor rotor 331. The position/orientation of the rotor's poles relative to the rotating magnetic field generator (coil assembly 224) is measured by back EMF, a rotary encoder, a hall effect sensor 225 (FIG. 5A), or the like. For instance, a Hall effect sensor mounted on the coil windings may be used to supply the microprocessor a count, a tachometer signal, or rotor position, allowing low-cost closed-loop control of the rotor speed. Brushless motors of this type are typically 85-90% or more efficient, and run very cool. While there may be variations in construction, the face-to-face stator coils and flat rotor plate shown in FIGS. 5A-5C provide a compact design. In addition, more coils and/or Hall effect sensors may be used.

Figure 6:
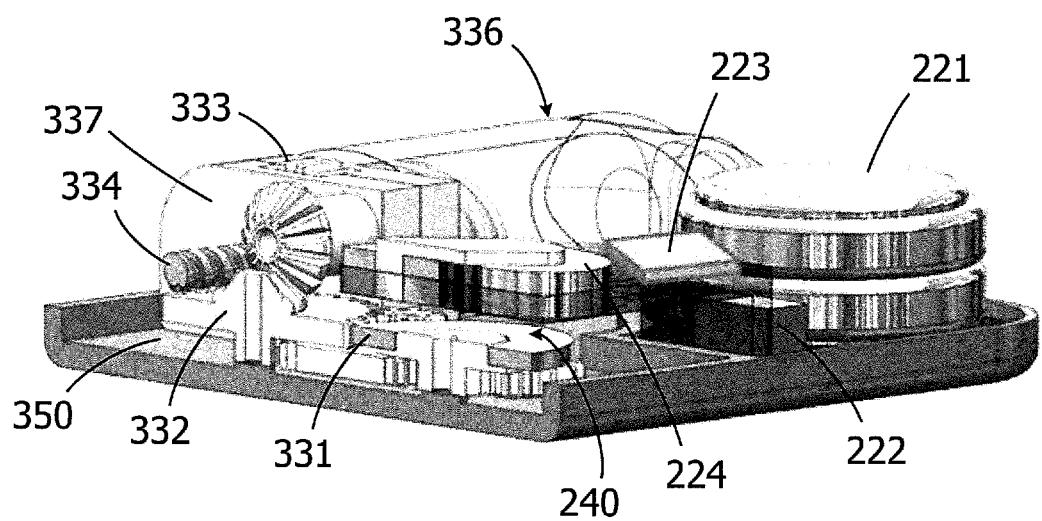
FIG. 6 is a perspective section view of components of the exemplary infusion pump system of FIG. 5A, revealing a gap between certain components of the durable and disposable assemblies.

As can best be seen in FIG. 6, between the motor coil assembly 224 and motor rotor 331 is a gap 240. Some or all of the gap 240 may be defined by (and occupied by) portions of the housing 202 and the cover 302, i.e., the housing bottom wall 206a and the cover top wall 304b in the illustrated implementation. In other implementations, the gap 240 between the between the motor coil assembly 224 and motor rotor 331 may be occupied by only a portion of the durable assembly housing, or only a portion of the disposably assembly cover, or no structure at all and may simply be an air gap. The size of the gap, which is defined by the distance between the motor coil assembly 224 and the motor rotor 331, is typically about 0.5 mm to 2.0 mm. As such, there is no gear engagement or other mechanical connection between the durable assembly 200 and disposable assembly 300. And as described earlier, all electronics may be positioned within the durable assembly 200, with the energy needed by the disposable assembly 300 transferred by electromagnetic torque coupling, which is a coupling without direct mechanical coupling or electrical contact from the durable assembly 200. This exemplary design affords the additional advantage of being relatively simple to make waterproof, or at least water resistant.

As described above, rotation of motor rotor 331 drives gear train 332, causing rotation of lead screw drive gear 333, which in turn affects translation of the lead screw 334 and plunger 335, which is attached to lead screw 334. In this manner, electromagnetically generated torque is created when electromagnetic energy supplied by durable assembly 200 is transformed into mechanical forces within the disposable assembly 300 that advance plunger 335. A ratchet (not shown) or other similar device may be used to prevent back drive of gear train 332. As plunger 335 is driven through reservoir 336, medicament is dispensed precisely, corresponding to the precision movements of the gears and motor rotor. With the entire gear train, lead screw drive gear, lead screw, and plunger all permanently contained in the disposable assembly 300, there is no need to retract any plunger components into the durable assembly 200 prior to separation from the disposable assembly 300. As a result, a further advantage of this exemplary design is greatly reduced energy consumption, which allows use of, for instance, a primary battery(ies) as a power source.

Figure 8:
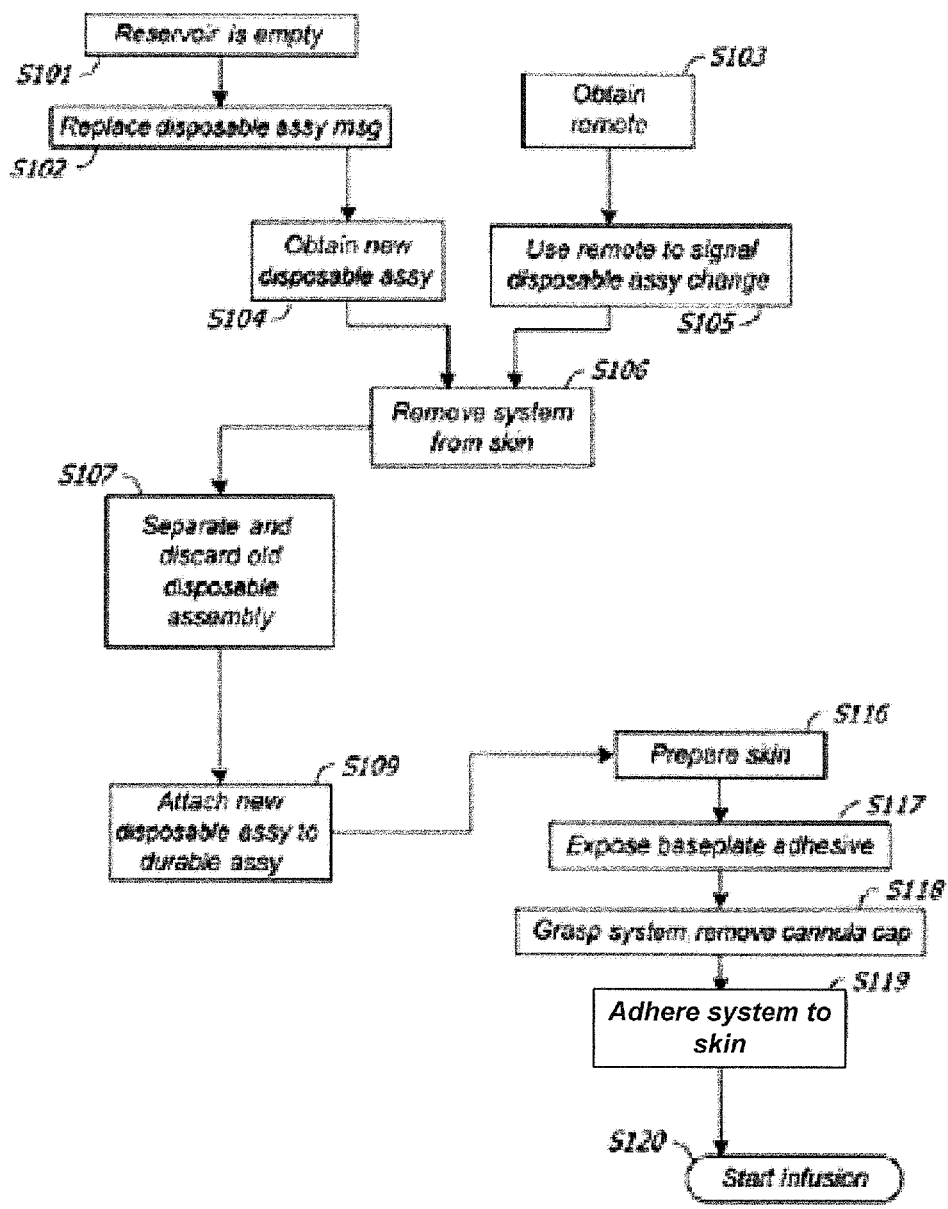
FIG. 8 is a flow chart illustrating an exemplary disposable assembly removal and replacement method.

Use of an exemplary system 100 will now be described. At the most basic level, a patient's use of the exemplary infusion pump systems (e.g., system 100 in FIGS. 1A-2B) involves obtaining a new disposable assembly 300, connecting the disposable assembly to the durable assembly 200, peeling the liner from the baseplate adhesive layer, gaining subcutaneous access, and initiating a medicament delivery operation. In some instances, use may involve additional steps such as attaching a cannula to connector 380 of the disposable assembly and removing a cannula cap, if necessary. Various aspects of the basic operation of the present systems are described below. Operation of a system does not necessarily require all of the steps each time the system is deployed, and the order of some of the steps may be changed. Operation is also discussed below, in the exemplary context of the above-described durable assembly 200 and disposable assembly 300 used as a patch pump, through the use of a flow chart (FIG. 8). The discussion is, however, equally applicable to other patch pump implementations, as well as to pocket pump implementations with minor variations. Also, unless otherwise indicated, the actions and determinations performed by the durable assembly 200 are controlled by the durable assembly microprocessor and further references to the controller are limited in the interest of brevity.

Referring to FIG. 8, use of the present systems may involve removal of a disposable assembly from a durable assembly and the replacement of the disposable assembly. This may occur when the medicament reservoir is empty (as described in more detail in U.S. patent application Ser. No. 12/890,207 and corresponding U.S. patent publication number 2012/0078170) (Step S101) and a "replace disposable assembly" message or alert is presented (Step S102), or when the durable assembly controller receives a user-initiated "replace disposable assembly" signal from a remote control 1000 (Step S103). The user may desire to replace a disposable assembly before the medicament reservoir is empty for a variety of reasons such as, for example, to accommodate the user's sleep or travel schedule, when the medicament exhibits a loss of effectiveness, when a dispensing problem arises, or due to a prescribed change in medicament.

The user may then obtain, possibly from storage in a refrigerator depending on medicament requirements, a new pre-filled disposable assembly 300 or may then obtain a new disposable assembly and fill the disposable assembly with medicament (Step S104). The durable assembly 200 and disposable assembly 300 may then be removed from the skin, separated, and the disposable assembly 300 discarded (Steps S106 and S107).

Figure 7:
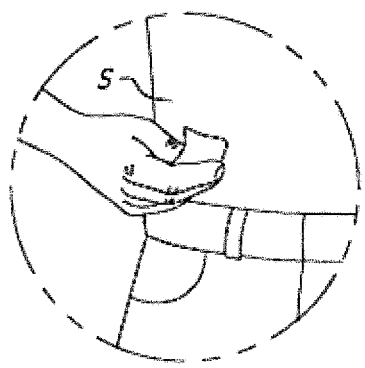
FIG. 7 is a front view showing a patient's skin being cleaned.

Next, the new disposable assembly 300 may be attached to the durable assembly 200 (Step S109). The user should clean the skin surface S onto which the baseplate 350 of disposable assembly 300 will be adhered (FIG. 7, and Step S116 of FIG. 8). Then the user peels off the baseplate adhesive liner to expose the baseplate adhesive layer (Step S117) and removes cannula cap (when present) (Step S118). In the exemplary use of FIG. 8, the disposable assembly 30 is supplied with a cannula in fluid communication with the reservoir storage volume. In other embodiments, a cannula inserter may be attached to the system, which may be triggered to insert the cannula after the system is placed against the skin. Exemplary inserters are described in U.S. patent publication number 2013/0138078.

Returning to the steps in FIG. 8, the system 100 including durable assembly 200 and disposable assembly 300 may be positioned over a suitable body location and pressed gently to adhere the adhesive layer to the skin surface S and, once the system has been adhered (Step S119), the inserter may be actuated to position the end of a cannula below the skin. It should be noted that in those implementations which do not include an inserter, and instead simply include a hollow needle (or a cannula and removable trocar arrangement) that projects outwardly from the bottom surface of the system, the user need only adhere the adhesive layer to position the needle or cannula below the skin. The trocar, if employed, may then be removed. Finally, if necessary, the remote control 1000 may be used to initiate a particular medicament delivery operation (Step S120). The delivery operation may follow a predetermined delivery profile (e.g. a particular basal rate, a series of time-spaced bolus deliveries, or some combination thereof) that is equated to motor rotor rotations, at particular rates and times, required to deliver medicament in accordance with the profile. Alternatively, the profile may be input by the user with the remote control 1000 and stored by the durable assembly microprocessor. For example, the remote control may store a number of different delivery profiles and bolus deliveries from which the patient can choose. Such profiles may correspond to, for example and depending on the medicament, days where vigorous exercise is expected, days where it is not, incidences of increased pain, etc. Alternatively, or in addition, the profile stored in the durable assembly microprocessor may be set by a clinician's programming unit. In such a case, as in the case of different disposable assemblies 300 provided with different specified delivery rates, a remote control may not be needed to initiate, e.g., basal delivery. The discussion above is also applicable to use of the "pocket pump" system as shown in FIG. 2B. Minor variations in the above-described procedure include, for example, use of an infusion set 382 instead of a cannula, attaching the infusion set to connector 380, potentially via an adapter (which may vary with the type of infusion set 382), and priming of the infusion set tube.

Figure 9:
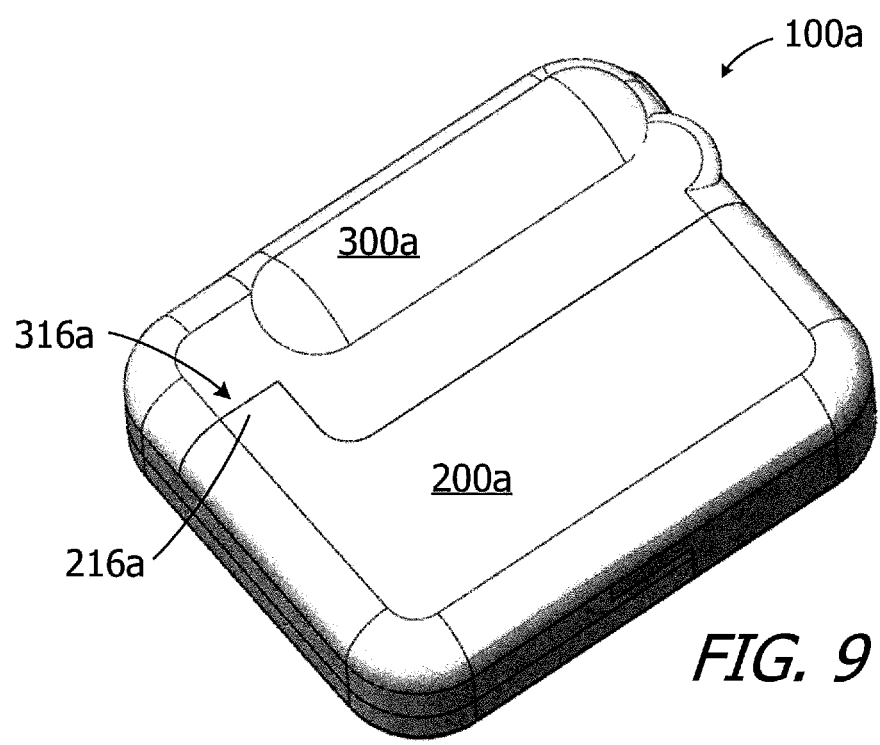
FIG. 9 is a perspective view of an exemplary infusion pump system in an assembled state.

Another exemplary ambulatory infusion system, which is generally represented by reference numeral 100a in FIG. 9, includes a durable assembly 200a and a disposable assembly 300a. System 100a is substantially similar to system 100. Here, however, the intersection of the top walls is primarily linear. Additionally, the disposable assembly 300a has a recess 316a which mates with a corresponding projection 216a on the durable assembly 200a. The projection 216a and recess 316a are located at the outer perimeter of the assembled system 100a.

The reservoirs may also be, but are not required to be, prefilled. Prefilled reservoirs are advantageous for a variety of reasons. By way of example, but not limitation, some users prefer to avoid reservoir filling procedures because they are inconvenient and tend to involve needles. User-based refilling also increases the likelihood that air bubbles will be introduced into the reservoir, while prefilling by the manufacturer of the reservoir and/or the medicament can be accomplished without any substantial introduction of air bubbles using, for example, a vacuum filling procedure. Nevertheless, user-filled reservoirs may be employed in some instances. A variety of exemplary medicament reservoirs, including those that include pressure sensors (such as for sensing occlusion) and other sensors, are described in more detail in aforementioned U.S. patent publication Nos. 2012/0078170, 2012/0184907, and 2013/0138078.

While a prefilled reservoir would greatly improve the ease of use of patch and pocket pump technology, there are several challenges to providing such prefilled reservoirs. By way of example but not limitation, long-term storage of insulin has traditionally used glass containers with bromobutyl rubber stoppers, and this has been applied to prefilled insulin pens using glass syringe barrels with bromobutyl plungers. The high coefficient of friction of bromobutyl on glass requires a coating of silicone oil on the interior of the reservoir, so the plunger may slide easily in the barrel during dispensing.

While successful in pens, this combination has several drawbacks, especially for low-cost patch and pocket pumps. For instance, glass is prone to fracture and flaking. In addition, glass is costly when tight tolerances must be maintained (e.g., for accurate dispensing from a small reservoir). Also, bromobutyl rubber compositions must be carefully controlled to prevent medicament contamination. Furthermore, silicone oil coatings require careful, controlled application, and occasionally result in medicament contamination. Although properly controlled application of silicone oil lowers the plunger "glide force", (also referred to as "running force," based on dynamic friction), the silicone oil tends to "squeeze out" from the sealing zone between the glass reservoir barrel and the rubber stopper/plunger over time, resulting in high "break force", (also referred to as "break-out force," based on static friction) during startup. Additionally, the glide force is quite variable within a single reservoir and the glide force and break force are quite variable from reservoir to reservoir (i.e., between reservoirs).

Accordingly, these glass/rubber/silicone oil based systems need to be designed to generate a high "break force" yet operate with a low "glide force". This results in more complex, larger, and more costly pumping systems.

As these materials were extended from insulin pens to prefilled reservoirs, attempts were made to replace the glass with cyclic olefin polymer (COP) or cyclic olefin copolymer (COC) and to replace the silicone oil layer with specialty coatings, such as Teflon and parylene, on the rubber plunger. While these coating materials achieved the goal of lowering the high coefficient of friction of rubber on COP/COC, the long-term stability of insulin solutions was compromised by water vapor migration out of the insulin solution and past the seal created by the coated rubber plunger. In a small, prefilled pump, such as a patch pump containing 400 microliters of insulin, the water lost from the insulin solution must be less than a few microliters per year. This is challenging with the configurations above.

A solution to this challenge is provided with a dual seal system. Each seal type has a distinct function and can therefore be designed ideally for that use. A first seal type is a static seal. When the pump is in storage, this seal minimizes water vapor loss. As will be seen below, this seal may be fixed into position within the reservoir assembly support block or on the plunger core. Since the static seal only functions during storage, it can be designed to function with relatively large contact stresses and soft, sticky materials, such as bromobutyl rubber, to seal against water vapor loss. A second seal type is a dynamic seal. This seal is designed as a low glide/break force seal that operates when the plunger is moving during dispensing, but it also must be compatible with long term insulin storage. When dispensing commences, the static seal automatically disengages, minimizing the forces required to move the plunger during dispensing.

Turning now to FIGS. 10-13, the exemplary pump reservoir assembly 400 illustrated therein, which may be employed in the exemplary ambulatory infusion system 100 described above or other infusion systems, includes a lead screw 434 engaged to a lead screw drive gear 433 and attached to plunger 435, which is positioned in a medicament reservoir 436. The reservoir 436 includes a barrel 438 with an inner surface 440 defining a fluid storage volume 442. The reservoir barrel 438, which may be formed from COP, COC, or the like, to maintain medicament (e.g., insulin) stability, is bonded or otherwise attached to support block 437 after the interior components (e.g., lead screw drive gear 433, lead screw 434, and plunger 435) are assembled. The end of the reservoir barrel 438 includes a connector 480.

The exemplary plunger 435 includes a plunger core 460 that is bonded or otherwise attached to lead screw 434 and carries at least one dynamic seal 462 that is in contact with the inner surface 440 of the reservoir barrel 438, where the plunger core 460 has an outer surface diameter and the inner surface 440 has an inner surface diameter. Plunger core 460 may be made of a relatively rigid material such as COP, COC, or the like, to maintain medicament (e.g., insulin) stability, and the dynamic seal(s) 462 may be made of a low friction resilient material, such as low friction plastic, parylene-coated rubber, Teflon-coated rubber, silicone-coated rubber, or the like. In the illustrated implementation, the dynamic seals 462 are o-ring seals. The plunger 435 slides within reservoir barrel 438 to dispense medicament. As described above in the context of infusion system 100, drive gear 433 rotates from torque supplied by a drive mechanism, such as magnetic motor rotor 331 and a gear train 332 in FIG. 2, to cause translation of the plunger 435.

Figure 10:
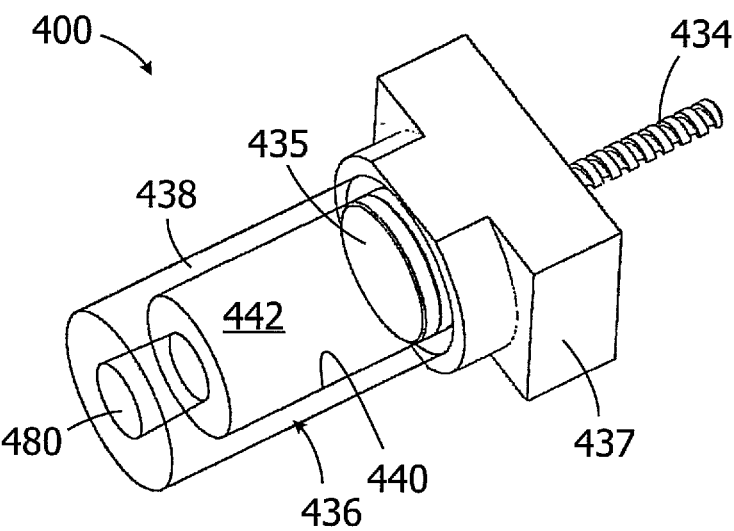
FIG. 10 is a perspective view of an exemplary reservoir assembly with the plunger in the full position.
Figure 11:
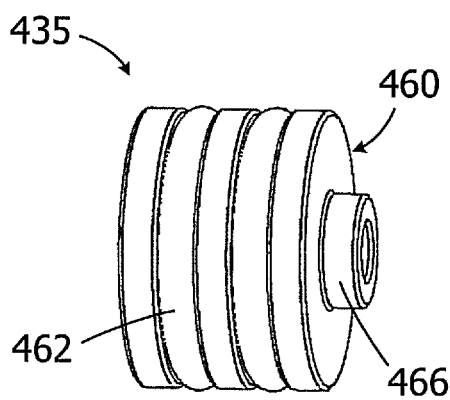
FIG. 11 is a perspective view of certain components of the reservoir assembly illustrated in FIG. 10.
Figure 13:
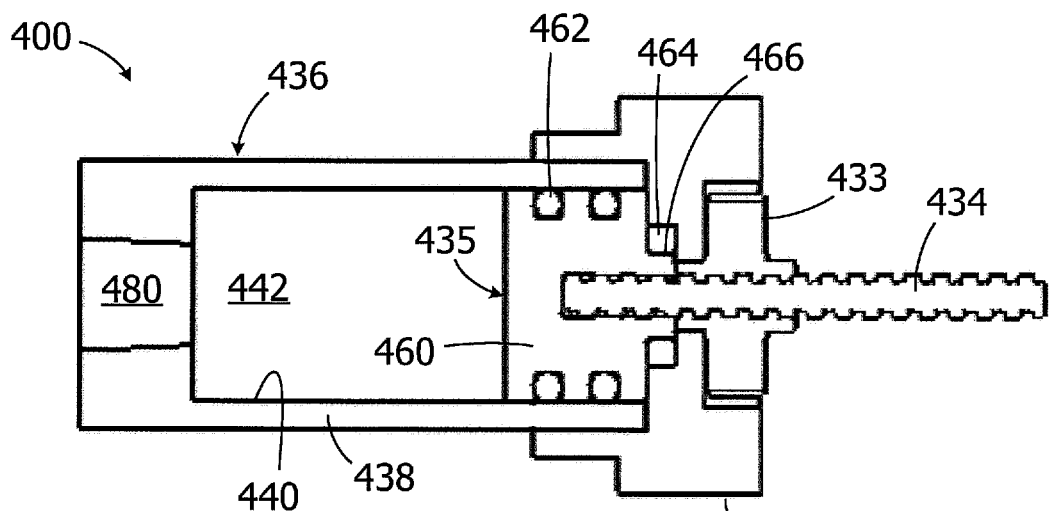
FIG. 13 is a section view of the reservoir assembly illustrated in FIG. 10.

As shown in FIGS. 10 and 13, the exemplary plunger 435 is in the "full position" when no medicament has been dispensed and the reservoir 436 is full. This may also be called the storage position, since the reservoir 436 is generally full during storage. The reservoir assembly 400 (as well as reservoir assemblies 400a and 400b (discussed below) may also be user-filled. In some instances where the reservoir assembly is user-filled, the plunger 435 will initially be located adjacent to the connector 480 and will move, in a direction opposite the dispensing direction, from there to the full position as the reservoir 436 is filled.

Figure 12:
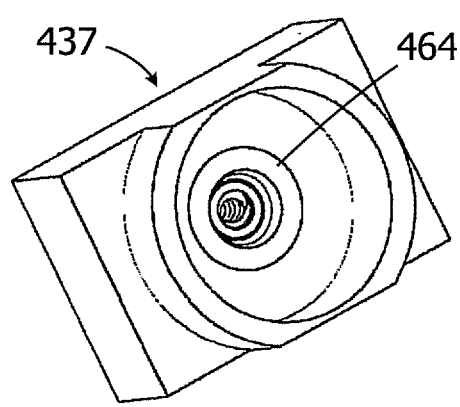
FIG. 12 is a perspective view of certain components of the reservoir assembly illustrated in FIG. 10.

When plunger 435 is in this full/storage position, at least one radial static seal 464 engages plunger core 460 to affect a static vapor seal. Radial static seal 464 may have various cross-sectional shapes and be attached to support block 437 in various ways. For instance, radial static seal 464 may be an O-ring having a static seal inner diameter and a static seal outer diameter. As another example, rather than fitting into a recess in support block 437, as shown in FIGS. 12 and 13, radial static seal 464 may be an O-ring that fits into an O-ring groove. In any case, the vapor seal may be achieved via an interference fit between radial static seal 464 and a static sealing surface 466 of plunger core 460. To achieve a seal via interference fit, radial static seal 464 may have a static seal inner diameter that is smaller than the outer diameter of the static sealing surface 466. The sealing surface 466 of plunger core 460 that is engaged by static seal(s) 464 may be designed to aid the vapor seal. For instance, this sealing surface 466 may be a slightly protruding circular surface. The interference between the plunger core sealing surface 466 and the radial static seal 464 causes elastomeric deformation of the seal 464 to create a vapor seal.

Figure 14:
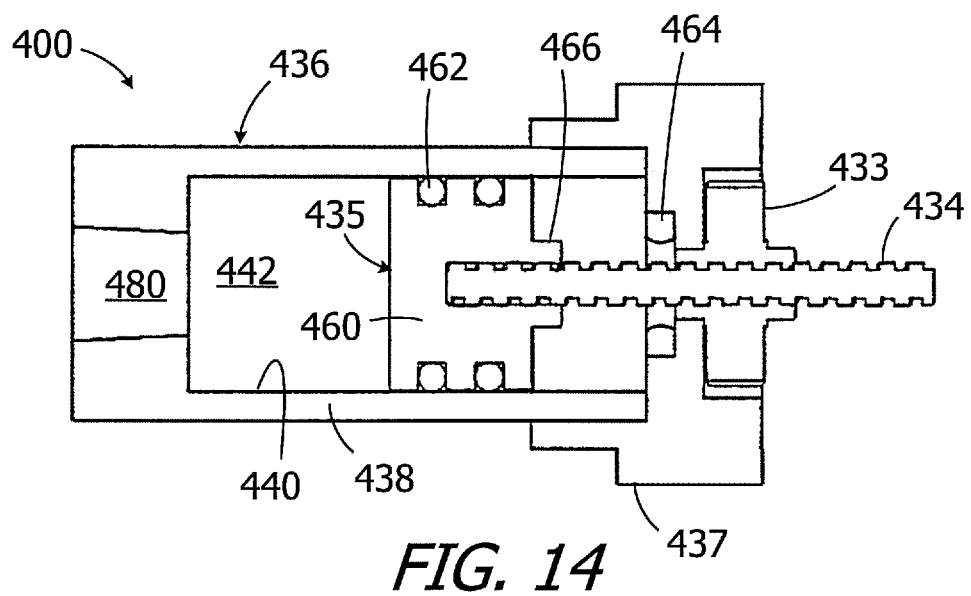
FIG. 14 is a section view of the reservoir assembly illustrated in FIG. 10 with the plunger not in the full position.
Figure 15:
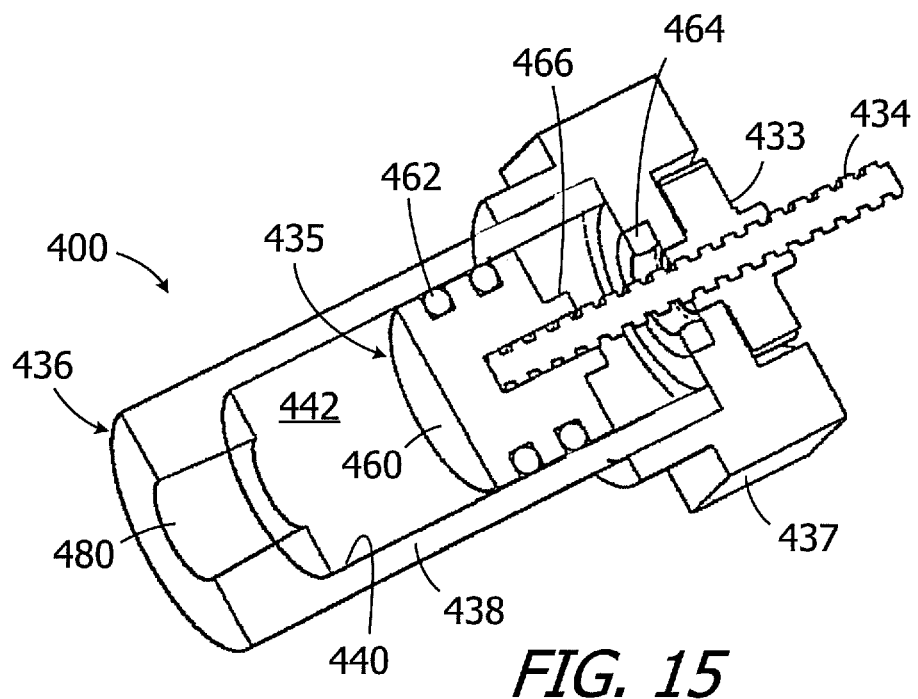
FIG. 15 is a section perspective view of the reservoir assembly illustrated in FIG. 10 with the plunger not in the full position.
Figure 16:
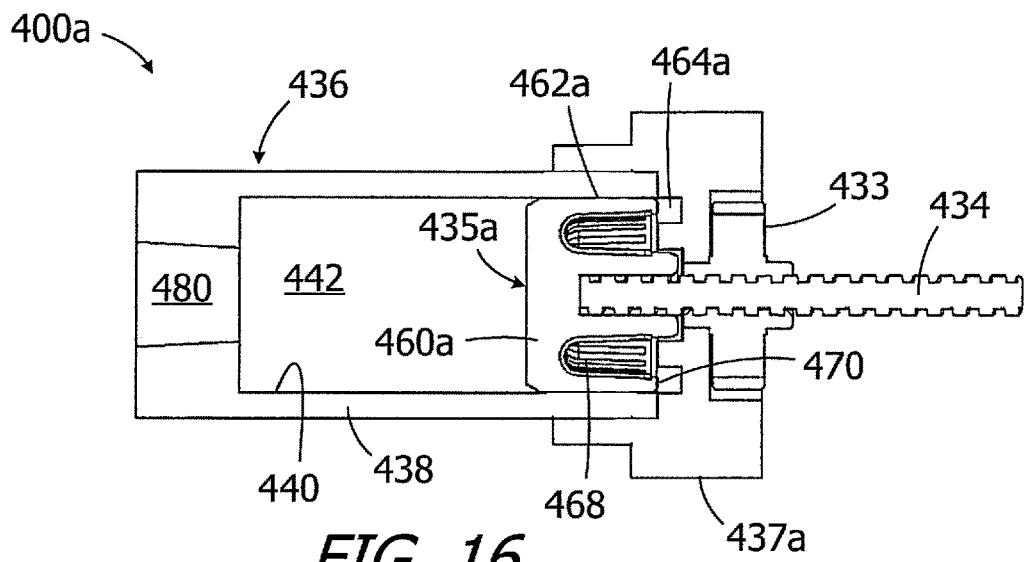
FIG. 16 is a perspective view of an exemplary reservoir assembly with the plunger in the full position.
Figure 17:
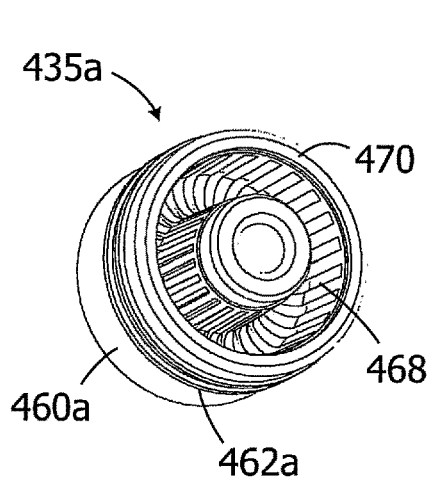
FIG. 17 is a perspective view of certain components of the reservoir assembly illustrated in FIG. 16.
Figure 18:
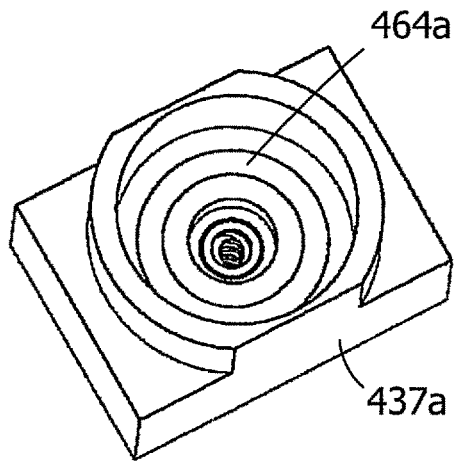
FIG. 18 is a perspective view of certain components of the reservoir assembly illustrated in FIG. 16.
Figure 19:
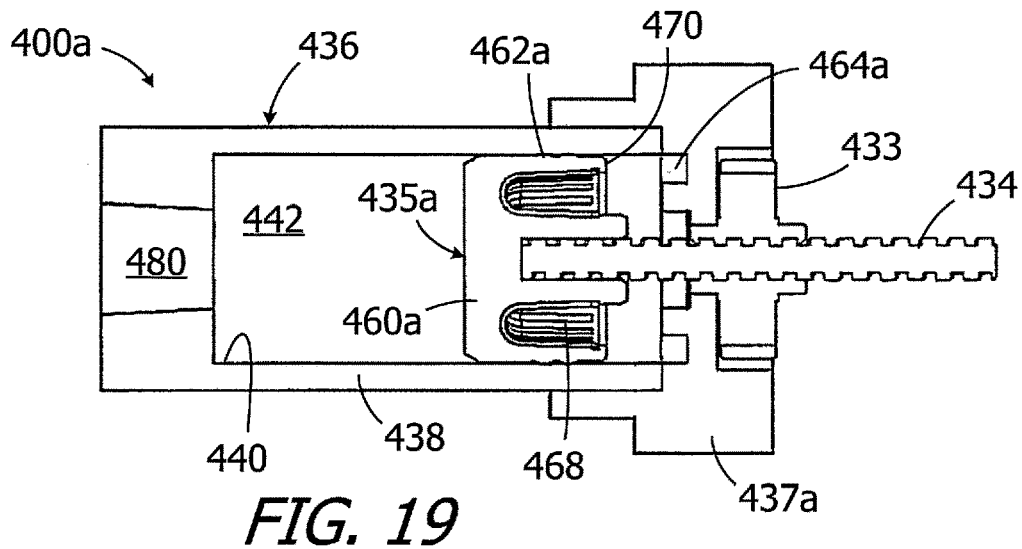
FIG. 19 is a section view of the reservoir assembly illustrated in FIG. 16 with the plunger not in the full position.

As shown in FIGS. 14 and 15, during dispensing of medicament, the plunger 435 moves in a dispensing direction away from the full position (FIGS. 10 and 13). For instance, in the orientation used for FIGS. 14 and 15, the plunger 435 translates left as medicament is dispensed. When dispensing begins, the plunger 435 begins to translate left and the sealing surface 466 of the plunger core 460 slides off the radial static seal(s) 464. As will be appreciated by those of skill in the art, the plunger 435 automatically disengages from the static vapor seal(s) 464, while contact between the dynamic seal(s) 462 and the inner surface 440 of the reservoir barrel 438 is maintained, when the plunger moves out of the full position (or "storage position"); that is, no additional steps or actions are required to deactivate the static vapor seal(s) 464 while the dynamic seal(s) 462 remain active, to separate sealing surface 466 from static seal(s) 464 while the dynamic seal(s) 462 remain in contact with the barrel inner surface 440, or to allow dispensing to begin. Put another way, the static vapor seal(s) 464 and the plunger 435 are disengaged from one another in response to a predetermined amount of movement of the plunger 435 in the dispensing direction out of the full position. The movement of the plunger 435 in the dispensing direction results in the static seal(s) 464 coming out of contact with the surface to which it is engaged to prevent vapor migration. In addition, the static seal(s) 464 are stationary; static seal(s) 464 do not need to change position in order for dispensing to begin or for the plunger 435 to move out of the full/storage position. As will also be appreciated by those of skill in the art, similar results may be obtained if the static seal(s) 464 are instead positioned on the plunger core 460 (for instance, around surface 466 of plunger core 460), so that the sealing surface is instead on support block 437. Here too, movement of the plunger 435 in the dispensing direction results in the static seal(s) 464 coming out of contact with the surface to which it is engaged to prevent vapor migration. In either case, radial static seal(s) 464 may be made of bromobutyl rubber or other relatively soft sealing material, for excellent long-term water vapor loss.

To lower contact forces and minimize friction to, in turn, lower break-out forces required to move away from the full/storage position, while still achieving acceptable sealing, the diameter of the sealing surface 466 of plunger core 460 may be kept as small as possible. When the static seal(s) 464 are engaged before dispensing begins, the radial sealing contact at sealing surface 466 provides an excellent vapor seal, which is especially important for long-term storage. Since the static seal(s) 464 are not engaged during dispensing, a low plunger 435 glide force may be achieved. This results in reduced energy consumption, which allows use of, for instance, primary battery(ies) as a power source. This is well suited to infusion systems that benefit from energy efficiency, such as the exemplary ambulatory infusion system 100 described above with reference to FIGS. 1A, 1B, and 2, since it is desirable to use no more energy than is actually needed.

Other embodiments of a dynamic seal combined with a static seal that disengages when dispensing commences, resulting in reduced forces and energy requirements, are possible. For instance, the exemplary reservoir assembly 400a illustrated in FIGS. 16-19 is substantially similar to reservoir assembly 400 and similar elements are represented by similar reference numerals. Here, however, the dynamic seals may be integral with the plunger core. To that end, the exemplary plunger 435a includes a plunger core 460a that may be molded or machined from a relatively rigid material (e.g., COP, COC, or the like) and includes integral sealing ridges 462a to achieve the dynamic seal. To ensure a seal between sealing ridges 462a and the inner surface 440 of reservoir barrel 438, a radial energizing spring 468 may be positioned within plunger core 460a. The radial energizing spring 468 radially deforms plunger core 460a to force sealing ridges 462a into a low friction, sealing contact with the inside surface 440 of reservoir barrel 438.

The exemplary static seal 464a may be one or more face-type static seals that engage(s) the rear surface of plunger core 460a when no medicament has been dispensed, the reservoir 436 is full (e.g., during storage), and the plunger 435a is in the "full position" or "storage position". Static face seal 464a may be made of bromobutyl rubber or other low-water-vapor-transmitting elastomers, for excellent long-term water vapor loss prevention. When plunger 435a is in the full position, the static face seal 464a and the rear surface of plunger core 460a are in contact, resulting in a vapor seal. In the example shown in FIG. 16, this seal is formed between the static face seal 460a and a static sealing surface 470 on the plunger core 460a.

As the plunger 435a slides within reservoir barrel 438 to dispense medicament, the plunger 435a moves away from the full/storage position, i.e., translates left (in the illustrated orientation) as medicament is dispensed. When dispensing begins, the plunger 435a begins to translate left (FIG. 19), and the sealing surface 470 of the plunger core 460a loses contact with static face seal(s) 464a. As will be appreciated by those of skill in the art, the plunger 435a automatically disengages from the static vapor seal(s) 464a, while contact between the dynamic seal(s) 462a and the inner surface 440 of the reservoir barrel 438 is maintained, when the plunger moves out of the full position (or "storage position"); that is, no additional steps or actions are required to deactivate the static face seal(s) 464a while the dynamic seal(s) 462a remain active, to separate static seal 464a from static sealing surface 270 while the dynamic seal(s) 462a remain in contact with the barrel inner surface 440, or to allow dispensing to begin. In addition, the static seal 464a is stationary; static seal 464a does not need to change position in order for dispensing to begin or for plunger 435a to move out of the full/storage position. Put another way, the static vapor seal(s) 464a and the plunger 435a are disengaged from one another in response to a predetermined amount of movement of the plunger 435a in the dispensing direction out of the full position.

Because static seal 464a is not engaged during dispensing, the glide force required to translate plunger 435a during dispensing is determined by the choice of materials for the reservoir barrel 438, plunger core 460a (when the dynamic seals are integral sealing ridges 462a), and the strength of radial energizing spring 468. As will also be appreciated by those of skill in the art, similar results may be obtained if static seal(s) 464a are instead positioned on the back side of the plunger core 460a (i.e., the surface of plunger core 460a that faces support block 437a), so that the sealing surface is instead on the surface of support block 437a that faces the back surface of plunger core 460a.

When the plunger 435a translates left (in the illustrated orientation) as dispensing begins, the static sealing surface 470 of plunger core 460a loses contact with static face seal 464a with minimal break-force required. In some instances, however, it may be desired to include a helper spring to assist disengagement of the plunger 435a from the static face seal 464a (or from radial static seal 464), or to aid the break force required for dynamic sealing ridges 462a (or for dynamic seal(s) 462), or to help with some combination of these. To that end, and referring to FIGS. 20-23, the exemplary reservoir assembly 400b is substantially similar to reservoir assembly 400a and similar elements are represented by similar reference numerals. Here, however, a helper spring 472 provides a force in just the small fraction of the distance that the plunger 435a travels through a reservoir barrel 438, such as only in about the first 1 mm, and then may lose contact with the plunger 435a. The helper spring 472 may be a disk spring (a.k.a., conical spring, conical washer, or Bellville spring). Multiple other spring types are possible, such as a coil spring, leaf spring, helical lock washer, curved washer, wave spring (a.k.a., wave washer or wavy washer), other compression spring or torsion spring, or the like.

Other positions for helper spring 240 (or similar spring that performs the same function) are also possible. For instance, a helper spring could be attached to a different portion of support block 437 and engage a different surface of plunger 435a. In other cases, a helper spring could be positioned on the back surface of plunger 435a and push against a surface on support block 437. In addition, as alluded to above, the helper spring can work with other types of static vapor seals, such as radial static seal 464, and/or with other types of dynamic seals, such as seal(s) 462. Furthermore, in some face-seal designs, the natural compressive elasticity of the seal may act as a spring trying to push the plunger 435a out. In such a case, the static face seal may act as the helper spring at an interface between the static sealing surface 470 and the static face seal 464a.

Use of a static seal(s) to address water vapor loss, in conjunction with separate dynamic seal(s) that are active during dispensing, allows optimization of the materials and material properties desired for the sealing surfaces, rather than trying to achieve both acceptable glide forces during dispensing and low water vapor loss during storage with just one type of sealing surface. Further, use of a static seal that automatically disengages when dispensing commences reduces the torque, and thus the energy, required to commence and continue dispensing. Thus, excellent dynamic sealing properties and excellent long-term static sealing properties may be achieved, while also conserving energy.

Various methodologies and systems are presented here in the context of the exemplary structures described in the preceding sections, and illustrated in the various figures, for the purpose of explanation only. Although the present methodologies and systems may employ the structures described above, they are not limited thereto. Additionally, embodiments of the present inventions may incorporate any one, combinations of less than all, or all of the methodologies or devices referenced above.

Although the inventions disclosed herein have been described in terms of the preferred embodiments above, numerous modifications and/or additions to the above-described preferred embodiments would be readily apparent to one skilled in the art. By way of example, but not limitation, the present reservoir assemblies may be incorporated into fully disposable infusion pumps. It is intended that the scope of the present inventions extends to all such modifications and/or additions and that the scope of the present inventions is limited solely by the claims set forth below or later added.

Finally, with respect to terminology that may be used herein, whether in the description or the claims, the following should be noted. The terms "comprising," "including," "carrying," "having," "containing," "involving," and the like are open-ended and mean "including but not limited to." Ordinal terms such as "first", "second", "third," do not, in and of themselves, connote any priority, precedence, or order of one element over another or temporal order in which steps of a method are performed. Instead, such terms are merely labels to distinguish one element having a certain name from another element having a same name (but for the ordinal term) to distinguish the elements. "And/or" means that the listed items are alternatives, but the alternatives also include any combination of the listed items. The terms "approximately," "about," "substantially" and "generally" allow for a certain amount of variation from any exact dimensions, measurements, and arrangements, and should be understood within the context of the description and operation of the invention as disclosed herein. Terms such as "top," "bottom," "above," and "below" are terms of convenience that denote the spatial relationships of parts relative to each other rather than to any specific spatial or gravitational orientation. Thus, the terms are intended to encompass an assembly of component parts regardless of whether the assembly is oriented in the particular orientation shown in the drawings and described in the specification, upside down from that orientation, or any other rotational variation therefrom.

What is claimed is:

1. An infusion pump reservoir assembly, comprising:
   a medicament reservoir comprising a reservoir barrel with an inner surface;
   a plunger moveable within the medicament reservoir in a dispensing direction from a full position; and
   a static seal that engages a sealing surface of a rear surface of the plunger that faces in a direction opposite the dispensing direction when the plunger is in the full position, wherein the static seal establishes an interference fit with elastomeric deformation with respect to the sealing surface when the plunger is in the full position,
   wherein the plunger and static seal are respectively configured and positioned relative to one another such that the static seal is disengaged from the sealing surface of the rear surface of the plunger in response to movement of the plunger in the dispensing direction from the full position, an inner diameter of the static seal is smaller than an outer diameter of the sealing surface, and wherein the plunger defines an outer surface diameter that is greater than an outer diameter of the static seal.

2. The infusion pump reservoir assembly of claim 1, wherein the static seal is a static vapor seal.

3. The infusion pump reservoir assembly of claim 1, wherein the static seal is stationary.

4. A method, comprising:
   engaging, in a medicament reservoir assembly of an infusion pump, a static seal with a sealing surface of a rear surface of a plunger that faces in a direction opposite a dispensing direction when the plunger is in a full position, wherein the static seal establishes an interference fit with elastomeric deformation with respect to the sealing surface when the plunger is in the full position; and
   disengaging the static seal from the sealing surface in response to movement in the dispensing direction of the plunger within a reservoir barrel of the medicament reservoir assembly from the full position, wherein an inner diameter of the static seal is smaller than an outer diameter of the sealing surface, and wherein the plunger defines an outer surface diameter that is greater than an outer diameter of the static seal.

5. The method of claim 4, wherein the static seal is a static vapor seal.

6. The method of claim 4, wherein the static seal is stationary.

* * * * *